United States Patent
Domogatskaya et al.

(10) Patent No.: US 8,951,799 B2
(45) Date of Patent: Feb. 10, 2015

(54) COMPOSITION AND METHOD FOR ENABLING PROLIFERATION OF PLURIPOTENT STEM CELLS

(75) Inventors: Anna Domogatskaya, Rönninge (SE); Sergey Rodin, Stockholm (SE); Karl Tryggvason, Djursholm (SE)

(73) Assignee: BioLamina AB, Sundbyberg (SE)

( * ) Notice: Subject to any disclaimer, the term of this patent is extended or adjusted under 35 U.S.C. 154(b) by 402 days.

(21) Appl. No.: 12/583,750

(22) Filed: Aug. 25, 2009

(65) Prior Publication Data

US 2010/0323443 A1 Dec. 23, 2010

Related U.S. Application Data

(63) Continuation-in-part of application No. 11/969,620, filed on Jan. 4, 2008, now Pat. No. 8,722,405.

(60) Provisional application No. 60/883,406, filed on Jan. 4, 2007, provisional application No. 61/091,531, filed on Aug. 25, 2008.

(51) Int. Cl.
*C12N 5/00* (2006.01)
*C12N 5/02* (2006.01)
*C12N 5/07* (2010.01)
*C12N 5/10* (2006.01)
*C12N 5/071* (2010.01)
*C12N 5/0735* (2010.01)

(52) U.S. Cl.
CPC .......... *C12N 5/0606* (2013.01); *C12N 2533/52* (2013.01)
USPC ............ 435/402; 435/354; 435/366; 435/377

(58) Field of Classification Search
CPC ................................ C12N 5/00; C12N 5/0606
USPC .................................. 435/377, 402, 354, 366
See application file for complete search history.

(56) References Cited

U.S. PATENT DOCUMENTS

2008/0213885 A1   9/2008   Tryggvason

FOREIGN PATENT DOCUMENTS

| WO | WO 2006/017370 A | 2/2006 |
| WO | WO 2008084401 | 7/2008 |
| WO | WO 2011/110886 A1 | 9/2011 |

OTHER PUBLICATIONS

Greenlea. Toxicology in Vitro, 19: 389-397, 2005.*
Lim et al. Proteomics, 2:1187-1203, 2002.*
Bajpai et al. Molecular Reproduction and Development, DOI 10.1002/mrd pp. 1-10, 2007.*
Hashimoto et al. Exp. Cell Res., 310: 256-269, 2005.*
Bair et al. Neoplasia, 7(4): 380-389, 2005.*
Nomizu et al. The Journal of Biological Chemistry, 273(46): 32491-32499, 1998.*
Beattie et al. Stem Cells, 23: 489-495, 2005.*
Millipore catalog. http://www.millipore.com/, accessed online on Feb. 24, 2009.*
Patarroyo et al. Seminars in Cancer Biology, 12: 197-207, 2002.*
Yu et al. Science, 318: 1917-1920, Dec. 21, 2007.*
Ogawa et al. Genes to Cells, 9: 471-477, 2004.*
Appendix B of Regenerative Medicine. Department of Health and Human Services. Aug. 2006, pp. 1-7. </info/scireport/2006report. htm>, accessed online on Dec. 13, 2010.*
Mallon et al. The Int. J. of Biochem. & Cell Bio., 38: 1063-1075, 2006.*
Amit et al. Dev. Biol., 227: 271-278, 2000.*
Cooper et al. J. of Cell Biology, 115(2): 843-850, 1991.*
Domogatskaya, Anna et al., "Laminin-511 but no -322, -111, or -411 enables mouse embryonic stem cell self-renewal in vitro" Stem Cells, Alphamed Press LNKD-DOI: 10.1634/Stemcells. 2007-0389, vol. 26, No. 11. pp. 2800-2809.
Meng Guoliang, et al., A novel method for generating xeno-free human feeder cells for human embryonic stem cell culture: Stem Cells and Development, Elsevier, NL LNKD-DOI:10.1089/SCD. 2007.0236, vol. 17, No, 3. pp. 413-422.
Ludwig, T. E., et al., "Derivation of human embryonic stem cells in defined conditions" Nature Biotechnology, Feb. 2006 Nature Publishing Group US, vol. 24, No. 2. pp. 185-187.
Miyazaki, T., et al., "Recombinant human laminin isoforms can support the undifferentiated growth of human embryonic stem cells" Biochemical and Biophysical Research Communications, Academic Press Inc., Orlando, FL, US LNKD- DOI:10.1016/J.BBRC.2008.07. 111, vol. 375, No. 1. pp. 27-32.
Rodin, Sergey, et al., "Long-term self-renewal of human pluripotent stem cells on human recombinant laminin-511." Nature Biotechnology, Jun. 2010 LNKD-PUBMED: 20512123, vol. 28, No. 7. pp. 611-615.
International Search Report dated Jun. 30, 2010.
Kortesmaa, J., et al. (2000); Recombinant laminin-8 (alpha(4)beta(1)gamma(1)). Production, purification, and interactions with integrins. J Biol Chem 275, 14853-14859.
Doi, M., et al. (2002); Recombinant human laminin-10 (alpha5beta1gamma1); Production, purification, and migration-promoting activity on vascular endothelial cells. J Biol Chem 277, 12741-12748.
Wartiovaara, J. et al. (2004); Nephrin strands contribute to a porous slip diaphragm scaffold as revealed by electron tomography. J. Clin. Invest. 114: 1476-1483 (2004).

(Continued)

*Primary Examiner* — Thaian N Ton
(74) *Attorney, Agent, or Firm* — Richard M. Klein; Fay Sharpe LLP

(57) ABSTRACT

The present disclosure is directed to the development of compositions, such as extracellular matrices, and processes for using the same, that both maintain stem cells in vitro pluripotency and enable self-renewal. In this regard, it has been discovered that when pluripotent mouse and human embryonic stem cells are cultured on plates coated with recombinant laminin-10 (laminin-511) or their functional domains, in the absence of differentiation inhibitors or feeder cells, the embryonic stem cells proliferated and maintained their pluripotency.

18 Claims, 24 Drawing Sheets
(10 of 24 Drawing Sheet(s) Filed in Color)

(56) References Cited

OTHER PUBLICATIONS

Tryggvason, K et al. (2006); Mechanisms of Disease: Hereditary Proteinuria Syndromes and Mechanisms of Proteinuria. N Engl J Med, vol. 354: 1387-1407 (Mar. 30, 2006).
Hudson, B.G. et al. (2003); Mechanisms of Disease: Alport's Syndrome, Goodpasture's Synhdrome, and Type IV Collagen. N Engl J Med, vol. 348: 2543-2556 (Jun. 19, 2003).
Wondimu, Z et al. (2005); Characterization of commercial laminin preparations from human placenta in comparison to recombinant laminins 2 ($\alpha 4\beta 1\gamma 1$), 10 ($\alpha 5\beta 1\gamma 1$). Matrix Biology 25 (2006) 89-93.
Thomson. Science, 282. 1145-1147, 1998.
Chu et al. J. Mol. Med., 76: 184-192, 1998.
Matrigel. BDBiosciences webpage. www.bdbiosciences.com, accessed online on Feb. 25, 2009.
Skottman, H., et al. (2006); The derivation of clinical-grade human embryonic stem cell lines; FEBS Lett 580, 2875-2878.
Hovatta, O., and Skottman, H. (2005); Feeder-free derivation of human embryonic stem-cell lines; Lancet 365, 1601-1603.
Xu, C., et al. (2001); Feeder-free growth of undifferentiated human embryonic stem cells; Nat Biotechnol 19, 971-974.
Klimanskaya, I., et al. (2005); Human embryonic stem cells derived without feeder cells; Lancet 365, 1636-1641.
Colognato, H., and Yurchenco, P. D. (2000); Form and function: the laminin family of heterotrimers; Dev Dyn 218, 213-234.
Domogatskaya et al., "Laminin-511 but not -322, -111, or 411 enables mouse embryonic stem cell self-renewal in vitro", Stem Cells (Dayton, Ohio), Nov. 2008, vol. 26, No. 11, Nov. 2008, pp. 2800-2809.
International Search Report dated Dec. 16, 2008.
Smith et al. J of Tiss. Cult. Methods. 13: 89-94, 1991.
Appendix F from the NIH website, definition of "Pluripotent Stem cell", accessed online on Feb. 25, 2009.
Aumailley, M. et al. (2005); A simplified laminin nomenclature; Matrix Biol 24, 326-332.
Williams R.L., et al. (1988); Myeloid leukemia inhibitory factor maintains the developmental potential of embryonic stem cells, Nature Dec. 15, 1988; 336(6200):684-7.
Richards, M., Fong, et al. (2002); Human feeders support prolonged undifferentiated growth of human inner cell masses and embryonic stem cells; Nat Biotechnol 20, 933-936.
Xu, R.H., et al. (2005); Basic FGF and suppression of BMP signaling sustain undifferentiated proliferation of human ES cells; Nat Methods 2, 185-190.
Cooper, A.R., and MacQueen, H.A. (1983); Subunits of laminin are differentially synthesized in mouse eggs and early embryos; Dev Biol 96, 467-471.
Dziadek, M., and Timpl, R. (1985); Expression of nidogen and laminin in basement membranes during mouse embryogenesis and in tetracarcinoma cells; Dev Biol 111, 372-382.
Evseenko, et al. "Identification of the critical extracellular matrix proteins that promote human embryonic stem cell assembly", Stem Cells and Development, vol. 18, No. 6, Jul. 2009, pp. 919-927.
International Search Report dated Nov. 11, 2011 for PCT/IB2011/000982.
Millipore Corporation catalog pages describing Catalog Item No. CC095, Mouse Laminin Purified Protein, pp. 1-4, accessed online at www.millipore.com/catalogue/item/cc095 on Jul. 16, 2012.

\* cited by examiner

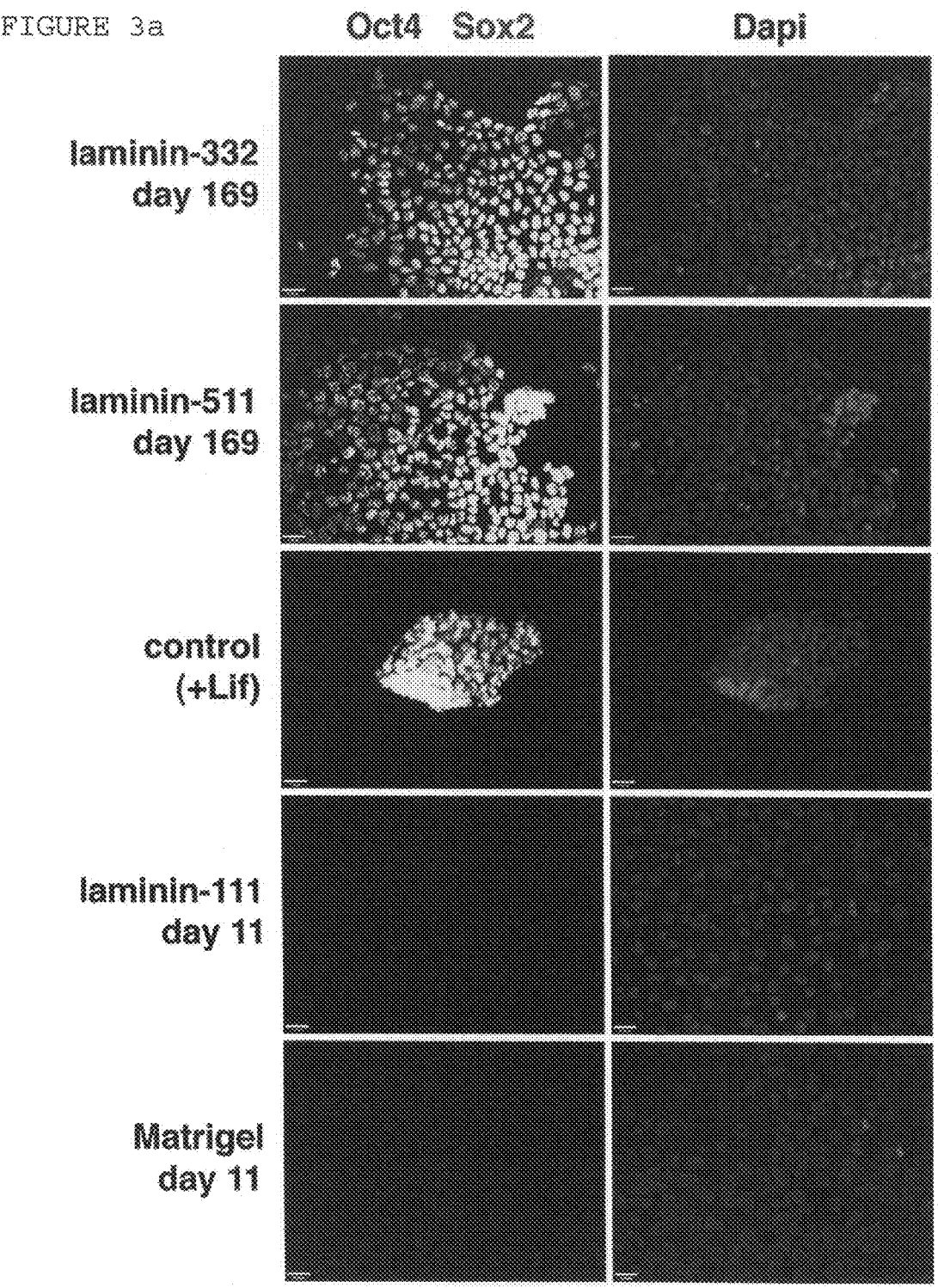

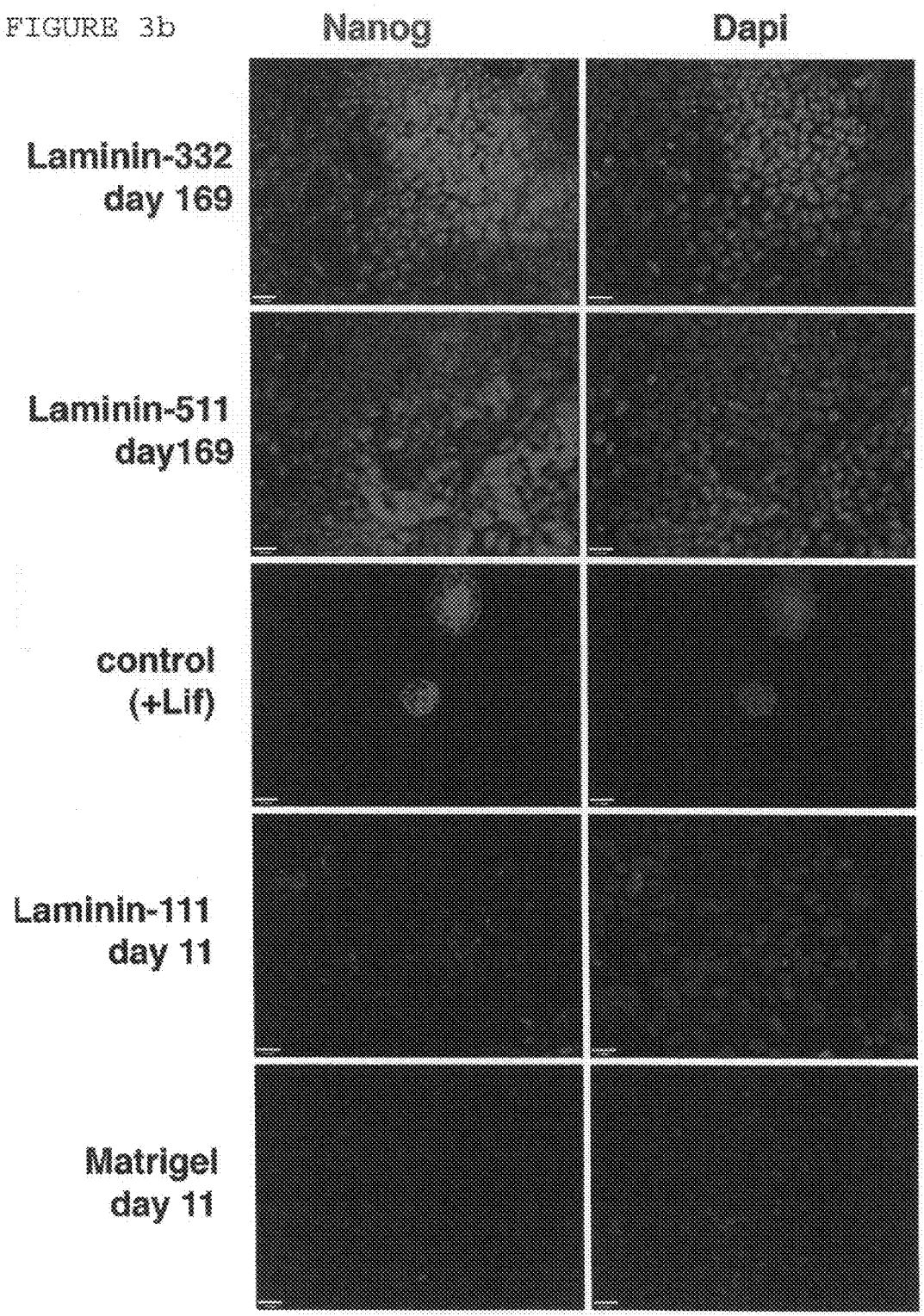

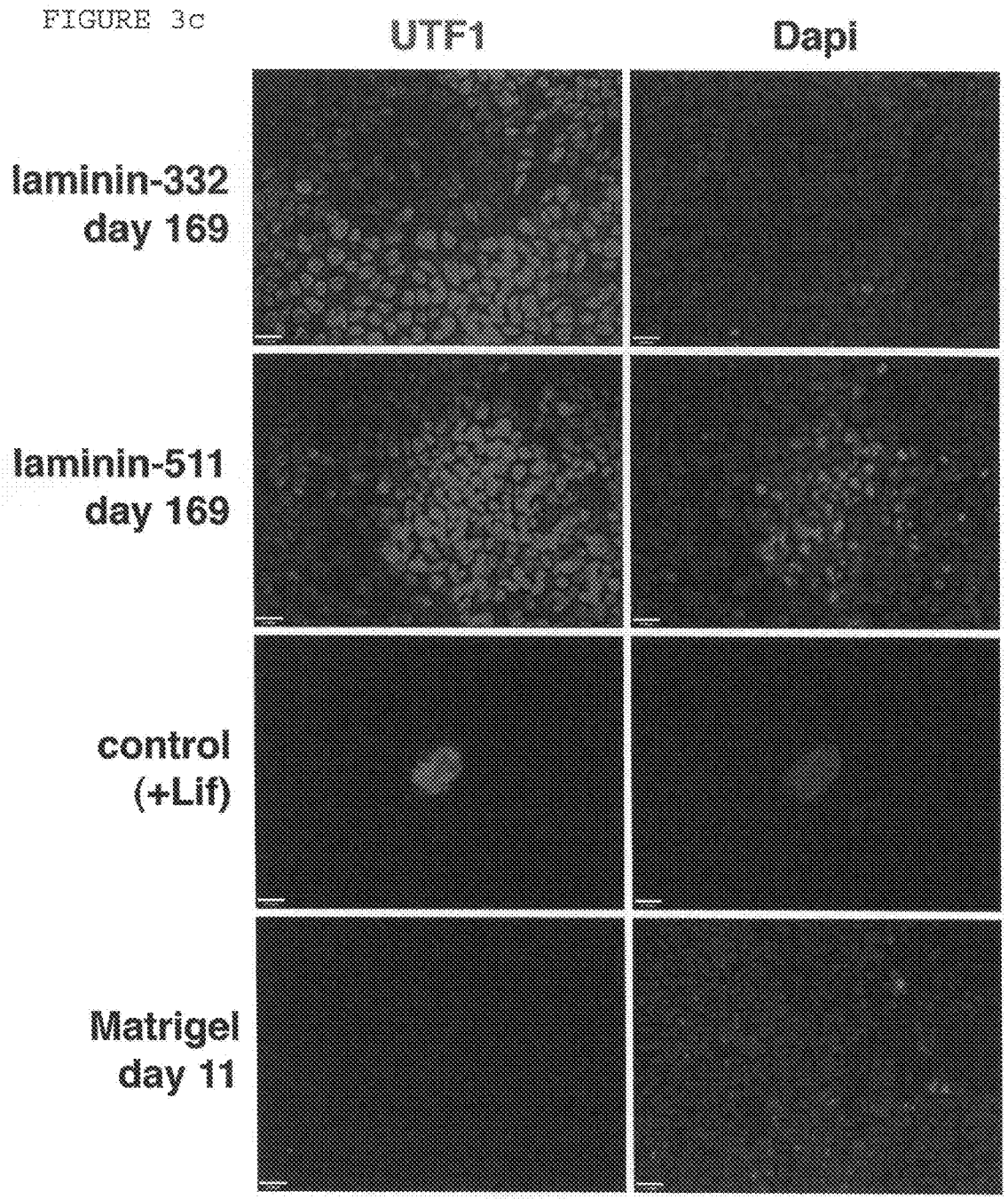

SEQUENCE LISTING

<160> NUMBER OF SEQ ID NOS: 32

<210> SEQ ID NO 1
<211> LENGTH: 24
<212> TYPE: DNA
<213> ORGANISM: Mus musculus

<400> SEQUENCE: 1
aggcccggaa gagaaagcga acta              24

<210> SEQ ID NO 2
<211> LENGTH: 24
<212> TYPE: DNA
<213> ORGANISM: Mus musculus

<400> SEQUENCE: 2 tggggcaga ggaaaggata cagc               24

<210> SEQ ID NO 3
<211> LENGTH: 22
<212> TYPE: DNA
<213> ORGANISM: Mus musculus

<400> SEQUENCE: 3
gtggaaactt ttgtccgaga cc                22

<210> SEQ ID NO 4
<211> LENGTH: 22
<212> TYPE: DNA
<213> ORGANISM: Mus musculus

<400> SEQUENCE: 4
tggagtggga ggaagaggta ac                22

<210> SEQ ID NO 5
<211> LENGTH: 21
<212> TYPE: DNA
<213> ORGANISM: Mus musculus

<400> SEQUENCE: 5
ctgcgtgtgc gtgctctgga c                 21

<210> SEQ ID NO 6
<211> LENGTH: 24
<212> TYPE: DNA
<213> ORGANISM: Mus musculus

<400> SEQUENCE: 6
cacctcagca aacagcttgt tctc              24

<210> SEQ ID NO 7
<211> LENGTH: 25
<212> TYPE: DNA
<213> ORGANISM: Mus musculus

<400> SEQUENCE: 7
gtggagattg ttgccatcaa cgacc             25

<210> SEQ ID NO 8

-continued

```
<211> LENGTH: 24
<212> TYPE: DNA
<213> ORGANISM: Mus musculus

<400> SEQUENCE: 8
ggctaagcag ttggtggtgc agga                                          24

<210> SEQ ID NO 9
<211> LENGTH: 23
<212> TYPE: DNA
<213> ORGANISM: Mus musculus

<400> SEQUENCE: 9
caagggtgag tagagagttc ggg                                           23

<210> SEQ ID NO 10
<211> LENGTH: 25
<212> TYPE: DNA
<213> ORGANISM: Mus musculus

<400> SEQUENCE: 10
tataacactg ttaggaaaga gggtc                                         25

<210> SEQ ID NO 11
<211> LENGTH: 21
<212> TYPE: DNA
<213> ORGANISM: Mus musculus

<400> SEQUENCE: 11
cggcccacgc atcccccatc c                                             21

<210> SEQ ID NO 12
<211> LENGTH: 24
<212> TYPE: DNA
<213> ORGANISM: Mus musculus

<400> SEQUENCE: 12
cagcggcctt ccaatctctg ttcc                                          24

<210> SEQ ID NO 13
<211> LENGTH: 24
<212> TYPE: DNA
<213> ORGANISM: Mus musculus

<400> SEQUENCE: 13
gctcatcgga acagctctcc aacc                                          24

<210> SEQ ID NO 14
<211> LENGTH: 24
<212> TYPE: DNA
<213> ORGANISM: Mus musculus

<400> SEQUENCE: 14
ggagaaccag aagacgagga cgtg                                          24

<210> SEQ ID NO 15
<211> LENGTH: 26
<212> TYPE: DNA
<213> ORGANISM: Mus musculus

<400> SEQUENCE: 15
gttttctgag ggatgaaacc tatgcc                                        26
```

```
<210> SEQ ID NO 16
<211> LENGTH: 24
<212> TYPE: DNA
<213> ORGANISM: Mus musculus

<400> SEQUENCE: 16
cgcccaaagc atcacgagtt ttgg                                          24

<210> SEQ ID NO 17
<211> LENGTH: 23
<212> TYPE: DNA
<213> ORGANISM: Mus musculus

<400> SEQUENCE: 17
ggcccctcat taagcctcag cgc                                           23

<210> SEQ ID NO 18
<211> LENGTH: 24
<212> TYPE: DNA
<213> ORGANISM: Mus musculus

<400> SEQUENCE: 18
gcaggacctg ctggcgtctt agat                                          24

<210> SEQ ID NO 19
<211> LENGTH: 20
<212> TYPE: DNA
<213> ORGANISM: Homo sapiens

<400> SEQUENCE: 19
cgaccatctg ccgctttgag                                               20

<210> SEQ ID NO 20
<211> LENGTH: 20
<212> TYPE: DNA
<213> ORGANISM: Homo sapiens

<400> SEQUENCE: 20
ccccctgtcc cccattccta                                               20

<210> SEQ ID NO 21
<211> LENGTH: 26
<212> TYPE: DNA
<213> ORGANISM: Homo sapiens

<400> SEQUENCE: 21
agcatccgac tgtaaagaat cttcac                                        26

<210> SEQ ID NO 22
<211> LENGTH: 24
<212> TYPE: DNA
<213> ORGANISM: Homo sapiens

<400> SEQUENCE: 22
cggccagttg tttttctgcc acct                                          24

<210> SEQ ID NO 23
<211> LENGTH: 20
<212> TYPE: DNA
<213> ORGANISM: Homo sapiens

<400> SEQUENCE: 23
gaaggtgaag gtcggagtca                                               20
```

-continued

<210> SEQ ID NO 24
<211> LENGTH: 20
<212> TYPE: DNA
<213> ORGANISM: Homo sapiens

<400> SEQUENCE: 24
ttcacaccca tgacgaacat                                              20

<210> SEQ ID NO 25
<211> LENGTH: 22
<212> TYPE: DNA
<213> ORGANISM: Homo sapiens

<400> SEQUENCE: 25
aacagacaca gccctcacaa ac                                           22

<210> SEQ ID NO 26
<211> LENGTH: 23
<212> TYPE: DNA
<213> ORGANISM: Homo sapiens

<400> SEQUENCE: 26
cgggaacttg aactggaact gac                                          23

<210> SEQ ID NO 27
<211> LENGTH: 20
<212> TYPE: DNA
<213> ORGANISM: Homo sapiens

<400> SEQUENCE: 27
ctttgggctg ctcgctatga                                              20

<210> SEQ ID NO 28
<211> LENGTH: 20
<212> TYPE: DNA
<213> ORGANISM: Homo sapiens

<400> SEQUENCE: 28
tggcttggaa agttcgggtc                                              20

<210> SEQ ID NO 29
<211> LENGTH: 20
<212> TYPE: DNA
<213> ORGANISM: Homo sapiens

<400> SEQUENCE: 29
gaaggtggat ctcaggtagc                                              20

<210> SEQ ID NO 30
<211> LENGTH: 21
<212> TYPE: DNA
<213> ORGANISM: Homo sapiens

<400> SEQUENCE: 30
catctcattg gtgagctcct t                                            21

<210> SEQ ID NO 31
<211> LENGTH: 24
<212> TYPE: DNA
<213> ORGANISM: Homo sapiens

<400> SEQUENCE: 31
ctcactttcc tccgcgttgc ttcc                                         24

```
<210> SEQ ID NO 32
<211> LENGTH: 24
<212> TYPE: DNA
<213> ORGANISM: Homo sapiens

<400> SEQUENCE: 32
tgccctggtc tttgtccttc atcc                                          24
```

COMPOSITION AND METHOD FOR ENABLING PROLIFERATION OF PLURIPOTENT STEM CELLS

CROSS REFERENCE TO RELATED APPLICATIONS

This application is a continuation-in-part of U.S. patent application Ser. No. 11/969,620, filed Jan. 4, 2008, which claimed priority to U.S. Provisional Application Ser. No. 60/883,406, filed on Jan. 4, 2007.

This application also claims priority to U.S. Provisional Application Ser. No. 61/091,531, filed on Aug. 25, 2008.

All of these applications are fully incorporated herein by reference in their entirety.

BACKGROUND

The present disclosure relates, in various exemplary embodiments, generally to compositions and methods for enabling adhesion, proliferation and self-renewal maintenance of pluripotent, or undifferentiated, stem cells in vitro. These stem cells include embryonic stem cells, such as murine or human, induced pluripotent stem cells, and bone marrow stem cells.

A stem cell is an undifferentiated cell from which specialized cells are subsequently derived. Embryonic stem cells and induced pluripotent stem reprogrammed from differentiated cells possess extensive self-renewal capacity and pluripotency with the potential to differentiate into cells of all three germ layers. They are useful for therapeutic purposes and may provide unlimited sources of cells for tissue replacement therapies, drug screening, functional genomics and proteomics. (Skottman, H., Dilber, M. S., and Hovatta, O. (2006); The derivation of clinical-grade human embryonic stem cell lines; FEBS Lett 580, 2875-2878).

Murine pluripotent embryonic cells can be maintained in a pluripotent state in in vitro cell culture conditions in the presence of Leukemia Inhibitory Factor (LIF). (Williams R L, Hilton D J, Pease S, Willson T A, Stewart C L, Gearing D P, Wagner E F, Metcalf D, Nicola N A, Gough N M (1988); Myeloid leukemia inhibitory factor maintains the developmental potential of embryonic stem cells, Nature 1988 Dec. 15; 336(6200):684-7).

Additionally, murine pluripotent embryonic cells can be maintained in a pluripotent state in vitro when cultured on mouse embryonic fibroblasts as feeder cells. Human embryonic cells also require feeder cells for maintenance in a pluripotent state in vitro or differentiation inhibitors like Noggin and/or high doses of basic fibroblast growth factor (FGF) when cultured on Matrigel™ (see for review: Skottman, H., Dilber, M. S., and Hovatta, O. (2006); The derivation of clinical-grade human embryonic stem cell lines; FEBS Lett 580, 2875-2878). However, the use of feeder cells has a number of drawbacks. For example, feeder cells can contain pathogens, such as viruses that can infect the stem cells (Hovatta, O., and Skottman, H. (2005); Feeder-free derivation of human embryonic stem-cell lines; Lancet 365, 1601-1603; Skottman, H., Dilber, M. S., and Hovatta, O. (2006); The derivation of clinical-grade human embryonic stem cell lines; FEBS Lett 580, 2875-2878).

Feeder-free systems that support human embryonic stem cell self-renewal require either i) Matrigel™ (Richards, M., Fong, C. Y., Chan, W. K., Wong, P. C., and Bongso, A. (2002); Human feeders support prolonged undifferentiated growth of human inner cell masses and embryonic stem cells; Nat Biotechnol 20, 933-936); (Xu, C., Inokuma, M. S., Denham, J., Golds, K., Kundu, P., Gold, J. D., and Carpenter, M. K. (2001); Feeder-free growth of undifferentiated human embryonic stem cells; Nat Biotechnol 19, 971-974); (Xu, R. H., Peck, R. M., Li, D. S., Feng, X., Ludwig, T., and Thomson, J. A. (2005); Basic FGF and suppression of BMP signaling sustain undifferentiated proliferation of human embryonic stem cells; Nat Methods 2, 185-190); or, ii) mouse feeders-derived extracellular matrix (Klimanskaya, I., Chung, Y., Meisner, L., Johnson, J., West, M. D., and Lanza, R. (2005); Human embryonic stem cells derived without feeder cells; Lancet 365, 1636-1641) as adhesive substrata. However, these coatings are of xenogenic origin and therefore cannot be used in clinics according to FDA requirements (Hovatta, O., and Skottman, H. (2005); Feeder-free derivation of human embryonic stem-cell lines; Lancet 365, 1601-1603). These coatings also fail to fulfill criteria of defined system and non-immunogenicity, importance of which is discussed in (Hovatta, O., and Skottman, H. (2005); Feeder-free derivation of human embryonic stem-cell lines; Lancet 365, 1601-1603; Skottman, H., Dilber, M. S., and Hovatta, O. (2006); The derivation of clinical-grade human embryonic stem cell lines; FEBS Lett 580, 2875-2878).

During mammalian embryonic development, a fertilized oocyte first divides into two cells, followed by another cell duplication to generate a four-cell embryo. At the four-cell stage, the embryonic cells are bound together with the help of cell membrane proteins and also the molecules of a new connective tissue (extracellular matrix). The first extracellular matrix molecules to appear are basement membrane proteins, such as laminin and proteoglycan (Cooper, A. R., and MacQueen, H. A. (1983); Subunits of laminin are differentially synthesized in mouse eggs and early embryos; Dev Biol 96, 467-471) (Dziadek, M., and Timpl, R. (1985); Expression of nidogen and laminin in basement membranes during mouse embryogenesis and in teratocarcinoma cells; Dev Biol 111, 372-382). Subsequently, the embryonic cells start to differentiate into the three germ cell layers; ectoderm, endoderm and mesoderm, with initiation of morphogenesis. The extracellular matrix molecules, such as laminins are responsible for interactions with cell surface receptors, thus regulating cell behavior such as adhesion, proliferation, migration and differentiation (Colognato, H., and Yurchenco, P. D. (2000); Form and function: the laminin family of heterotrimers; Dev Dyn 218, 213-234), while other extracellular matrix components such as collagens of types I, II, III or IV primarily serve a mechanical supportive function (Aumailley, M., and Gayraud, B. (1998); Structure and biological activity of the extracellular matrix; J Mol Med 76, 253-265).

Extracellular matrix derived from murine fibroblasts, in combination with soluble differentiation inhibitors may be an adequate replacement for feeder cells (Klimanskaya, I., Chung, Y., Meisner, L., Johnson, J., West, M. D., and Lanza, R. (2005); Human embryonic stem cells derived without feeder cells; Lancet 365, 1636-1641), which demonstrates the critical role of extracellular matrix molecules. Laminins are large trimeric extracellular matrix proteins that are composed of alpha, beta, and gamma chains. There exist five different alpha chains, three beta chains and three gamma chains that in mouse and human tissues have been found in at least fifteen different combinations (Colognato, H., and Yurchenco, P. D. (2000); Form and function: the laminin family of heterotrimers; Dev Dyn 218, 213-234); (Aumailley, M., Bruckner-Tuderman, L., Carter, W. G., Deutzmann, R., Edgar, D., Ekblom, P., Engel, J., Engvall, E., Hohenester, E., Jones, J. C., et al. (2005); A simplified laminin nomenclature; Matrix Biol 24, 326-332). These hetertrimeric molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains (laminin nomenclature: (Aumailley, M., Bruckner-Tuderman, L., Carter, W. G., Deutzmann, R., Edgar, D., Ekblom, P., Engel, J., Engvall, E., Hohenester, E., Jones, J. C., et al. (2005); A simplified laminin nomenclature; Matrix Biol 24, 326-332)).

The different isoforms are developmentally regulated and have tissue specific locations and functions. LN-111 (previously named laminin-1 or laminin) is present in the early embryo and later in certain epithelial cells and murine EHS sarcoma, but otherwise it is a rare isoform in vivo. LN-511 (LN-10) is the most common form found in basement membranes of the early embryo and most adult tissues. Importantly, it is found in the extracellular matrix between cells of the inner cell mass of blastocysts. Laminins are cell type-specific mediators regulating cell adhesion, proliferation, migration, and resistance to apoptosis. Mutations in most laminin chains result in severe pathologies and mortality.

Most laminin isoforms, except for laminin-111, are difficult to extract and purify in native forms from tissues due to extensive crosslinking with other laminins or other macromolecules. Only recently human/mouse hybrid LN-111 (LN-1), and human LN-211 (LN-2), LN-332 (LN-5) specific for epithelial basement membranes, LN-411 (LN-8) common in vascular basement membranes and the ubiquitous LN-511 (LN-10) have been successfully produced as recombinant proteins. It is also possible to isolate some laminin isoforms like LN-332 (LN-5) from cultured cells, but only in low quantities.

There is a need to develop defined feeder cell free in vitro culture systems for establishment and maintenance of undifferentiated mammalian embryonic stem cells, induced pluripotent stem cells, as well as bone marrow stem cells. A major problem of embryonic stem cell cultures is the lack of appropriate surface coatings, particularly regarding human embryonic stem cells. Although defined xeno-free embryonic stem cell culture media have successfully been developed for human embryonic stem cells, researchers are still looking for defined xeno-free non-immunogenic culture plate coatings that do not induce cellular differentiation. Adhesive surface coatings are usually based on various combinations of extracellular matrix proteins, such as laminin-111, collagen IV, gelatin, fibronectin, or Matrigel™, most of which are undefined or not human. For instance, successfully used coatings, such as Matrigel™ prepared from the mouse EHS sarcoma, or extracellular matrix derived from mouse embryonic fibroblasts, are of undefined non-reproducible composition and derived from animal sources. Therefore, they are not applicable for clinical purposes.

Laminins that are central components of basement membranes (BM) are the first extracellular matrix molecules to contact cells in the early embryo. Expression of laminin chains has been shown to occur already at the 2-4 cell stage in mouse embryos. One of the laminins, laminin-511, contacts the inner cell mass of blastocysts which is the natural origin of embryonic stem cells. Laminins have been shown to influence cellular differentiation and migration, in addition to promoting adhesion and proliferation, while some other extracellular matrix molecules like collagens primarily provide adhesion and structural support functions. Thus laminins may be useful for culturing embryonic stem cells in vitro, as they are a natural part of the niche for their origin in vivo.

Notwithstanding the above, there continues to be a need for providing compositions and methods for culturing and growing embryonic stem cells. In this regard, providing compositions and methods for enabling the proliferation and survival of pluripotent stem cells in vitro without use of differentiation inhibitory agents such as LIF or feeder cells would be advantageous.

SUMMARY

The present disclosure is directed to the development of devices and compositions, such as extracellular matrices, and processes for using the same, for culturing and expanding stem cells in vitro in an undifferentiated state. Preferably, the stem cells are embryonic stem cells, such as murine or human embryonic stem cells. However, the present disclosure also includes the use of bone marrow stem cells and induced pluripotent stem cells (iPS cells) as well.

It has been found that certain laminins provide a defined and suitable extracellular matrix for the growth and proliferation of undifferentiated mouse and human embryonic stem cells in vitro. This is absent any feeder cells and/or differentiation inhibitors. For example, it has been discovered that when pluripotent mouse embryonic stem cells are cultured on plates coated with recombinant laminin-10 (laminin-511) or laminin-5 (laminin-332), the embryonic stem cells proliferate and maintain their pluripotency even in an absence of differentiation inhibitors.

Also, it has been found that when pluripotent human embryonic stem cells are cultured on plates coated with recombinant laminin-10 (laminin-511) in a chemically defined medium, such as an analog of mTeSR1, the cells can proliferate and maintain their pluripotency even in an absence of differentiation inhibitors.

Furthermore, it was found that certain laminin isoforms can either act as differentiation inductors, or sustain embryonic stem cell self-renewal. The results revealed that various laminin isoforms cause diverse effect on embryonic stem cells. LN-511 enabled mouse embryonic stem cell self-renewal for over 5 months in absence of any differentiation inhibitors. LN-332 enabled embryonic stem cell proliferation, but not pluripotency. LN-111 caused embryonic stem cell differentiation within 2 weeks. LN-411 was not capable of supporting embryonic stem cell survival.

These investigations were performed using both mouse and human embryonic stem cells. The results are generally applicable to all pluripotent stem cells regardless of their source. In particular, whether the stem cell is embryonic, adult, or induced is irrelevant; what is important is that they are pluripotent.

These and other non-limiting features of the present disclosure are discussed in more detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

FIGS. 3a-3d relate to a series of color photomicrographs (Immunofluorescence (×40)) demonstrating mouse embryonic stem cell self-renewal effect on laminins-332 and -511. FIG. 3a is directed to photomicrographs of immunofluorescence staining against pluripotency markers Oct4 and Sox2. Embryonic stem cells cultured in presence of LIF (control+LIF) express pluripotency marker Oct4 and Sox2 (control). After culturing on laminin-332 or laminin-511 in absence of LIF or any other differentiation inhibitor for 169 days, embryonic stem cells continue to express Oct4 (green) and Sox2 (red). It is noteworthy that after culturing for only 11 days on laminin-111 or on Matrigel™, embryonic stem cells cease to express Oct 4 and Sox2. Magnification 40×. Bar size 27 μm. FIG. 3b relates to photomicrography showing similar data of immunofluorescence staining against pluripotency marker Nanog. FIG. 3c shows similar data of immunofluorescence staining against pluripotency marker UTF1. FIG. 3d is directed to photomicrographs of immunofluorescence staining against pluripotency marker Oct4 (green) and differentiation marker Collagen IV (red), and presence of DNA (DAPI, blue) in embryonic stem cells cultured for on LN-511 for 169 days and on LN-111 for 11 days in absence of differentiation inhibitors. Embryonic stem cells cultured in presence of LIF on gelatin serve as positive control. Undifferentiated embryonic stem cells positive for Oct4 (LN-511 and control) did not express collagen IV, but cells differentiated on LN-111 were negative for Oct4 and strongly positive for collagen IV. Magnification ×40. Bar size is 27 μm.

FIG. 12 is a set of photos of chimeric mice generated from embryonic stem cells cultured on LN-511 in the absence of differentiation inhibitors, showing germ line transmission of the embryonic stem cells.

FIG. 14 is a set of photomicrographs showing immunofluorescent staining of embryonic stem cells cultured on LN-511 at both low and high magnification. The cells were stained for Oct4 (blue), integrin β1 (green), and f-actin (red) vs phase contrast (Nomarsky staining). Spread monolayer morphology of embryonic stem cells cultured on LN-511 strikingly differs from conventional dense cluster morphology of embryonic stem cells cultured in presence of LIF on gelatin. As a result, the embryonic stem cells are hardly visible in phase contrast, unlike clearly visible embryonic stem cell clusters grown in presence of LIF. Unusual morphology did not affect Oct4 expression in embryonic stem cells.

FIG. 16a is a graph showing the adhesion of embryonic stem cells to surfaces coated by different anti-integrin antibodies (experiment I). Bars represent (from left to right): control for 100% adhesion (Ctrl), β1 (BD Biosciences), α6, α5β1, αV, α2β1, α4, αVβ6, β2, and IgG. The positive control (Ctrl) relates to total number of cells introduced to the surface. IgG was used as negative control. Error bars show standard error (SEM, n=4). Statistical significance calculated by the Student t-test is shown as: (***) for P<0.001.

FIG. 16b is a graph showing the adhesion of embryonic stem cells to surface coated by different anti-integrin antibodies (experiment II). Bars represent (from left to right): control for 100% adhesion (ctrl), β1 (R&D Systems), β1+β3, β1 (BioLegend), β1+αV, α2β1, α3, α4, β2, β3 (BD Biosciences), β3 (BioLegend), and IgG. Error bars show standard error (SEM, n=4). Statistical significance calculated by the Student t-test is shown as: () for P<0.01 and (*) for P<0.001.

FIG. 16c is a graph showing the inhibition of embryonic stem cell adhesion to LN-511 by different anti-integrin antibodies (experiment I). Bars represent (from left to right): control for 100% inhibition (ctrl), β1 (BD Biosciences, from mouse), β1 (BD Biosciences, from Armenian hamster), α6, α6+αV, α3, α4, αV (BioLegend), αV (Chemicon), β2, β3 (BD Biosciences), β3 (BioLegend), β4, IgG. The control (ctrl) relates to absence of adherent cells. IgG was used as control for uninhibited cell adhesion. Error bars show standard error (SEM, n=4). Statistical significance calculated by the Student t-test is shown as: () for P<0.01 and (*) for P<0.001.

FIG. 16d is a graph showing the inhibition of embryonic stem cell adhesion to LN-511 by different anti-integrin antibodies (experiment II). Bars represent (from left to right): control for 100% inhibition (ctrl), α6, αV, α2β1, α3, α3 (BD Biosciences), α5β1, β4, IgG. The control (ctrl) relates to absence of adherent cells. IgG was used as control for uninhibited cell adhesion. Error bars show standard error (SEM, n=3). Statistical significance calculated by the Student t-test is shown as: (*) for P<0.05.

FIG. 16e is a graph showing that embryonic stem cell contact area with LN-511-coated surface is reduced after blocking of α6 integrin receptor by antibody. Error bars show standard error (SEM), number inside each bar shows number of independent measurements (n). Statistical significance calculated by the Student t-test is shown as: (***) for P<0.001.

FIG. 16f is a set of pictures showing immunofluorescence: integrin α6, αV, α5β1 co-expression with β1 integrin subunit in pluripotent (Sox2-positive) embryonic stem cells cultured on LN-511 (left) or in presence of LIF on gelatin (right). Magnification ×40. Bar size is 100 µm.

DETAILED DESCRIPTION

Figure 1A:
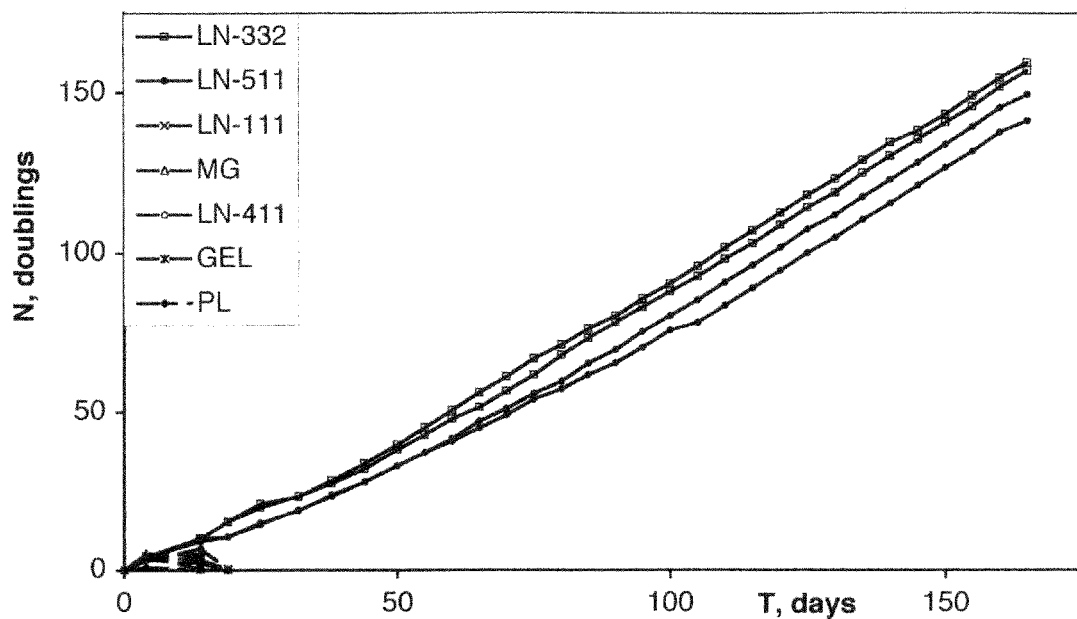
FIG. 1a is a graph showing the proliferation of mouse embryonic stem cells on laminins (LN), Matrigel™ (MG), gelatin (GEL) and poly-D-lysine (PL). Cells expanded on LN-332 and LN-511 for up to at least 169 days during which about 150 doublings in cell number occurred. In contrast, the cells did not self-renew on LN-111, LN-411, gelatin or poly-D-lysine.
Figure 5A:
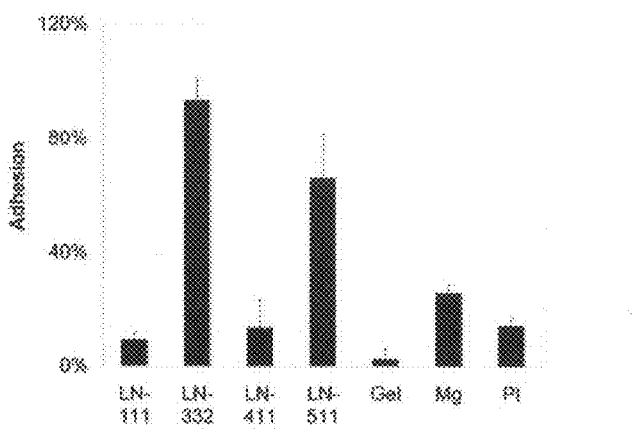
FIG. 5a is a graph showing adhesion of pluripotent mouse embryonic stem cells to different coating surfaces: laminin-111 (LN-111), laminin-332 (LN-332), laminin-411 (LN-411), laminin-511 (LN-511), Matrigel (MG), gelatin (GEL) and poly-D-lysin (PL). Values are shown as percentage of attached cells±standard deviation (STD).
Figure 5B:
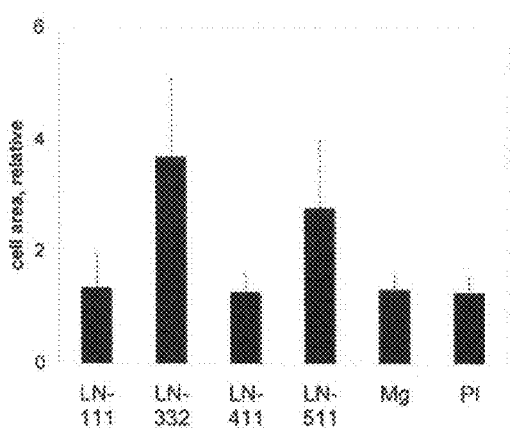
FIG. 5b is a graph showing spreading of pluripotent ESCs adhered to different coating surfaces. The area of cells that adhered to a certain coating was calculated as a measure of spreading efficacy. The areas are depicted as average relative areas±standard deviation (STD).
Figure 5C:
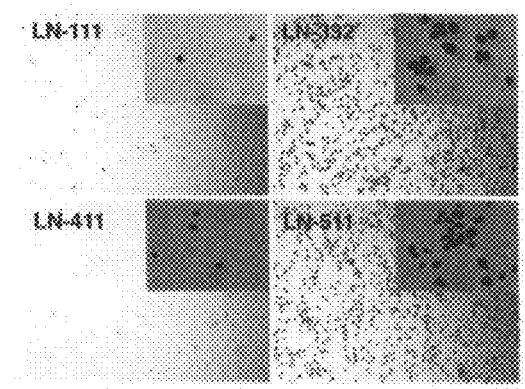
FIG. 5c is a series of four (4) micrographs showing embryonic stem cells adherent to different laminins after 1 hour incubation. Crystal violet staining, magnification (×5/×40). As indicated, laminin-332 and -511, unlike laminins-111 or -411, are highly adhesive for embryonic stem cells.
Figure 6:
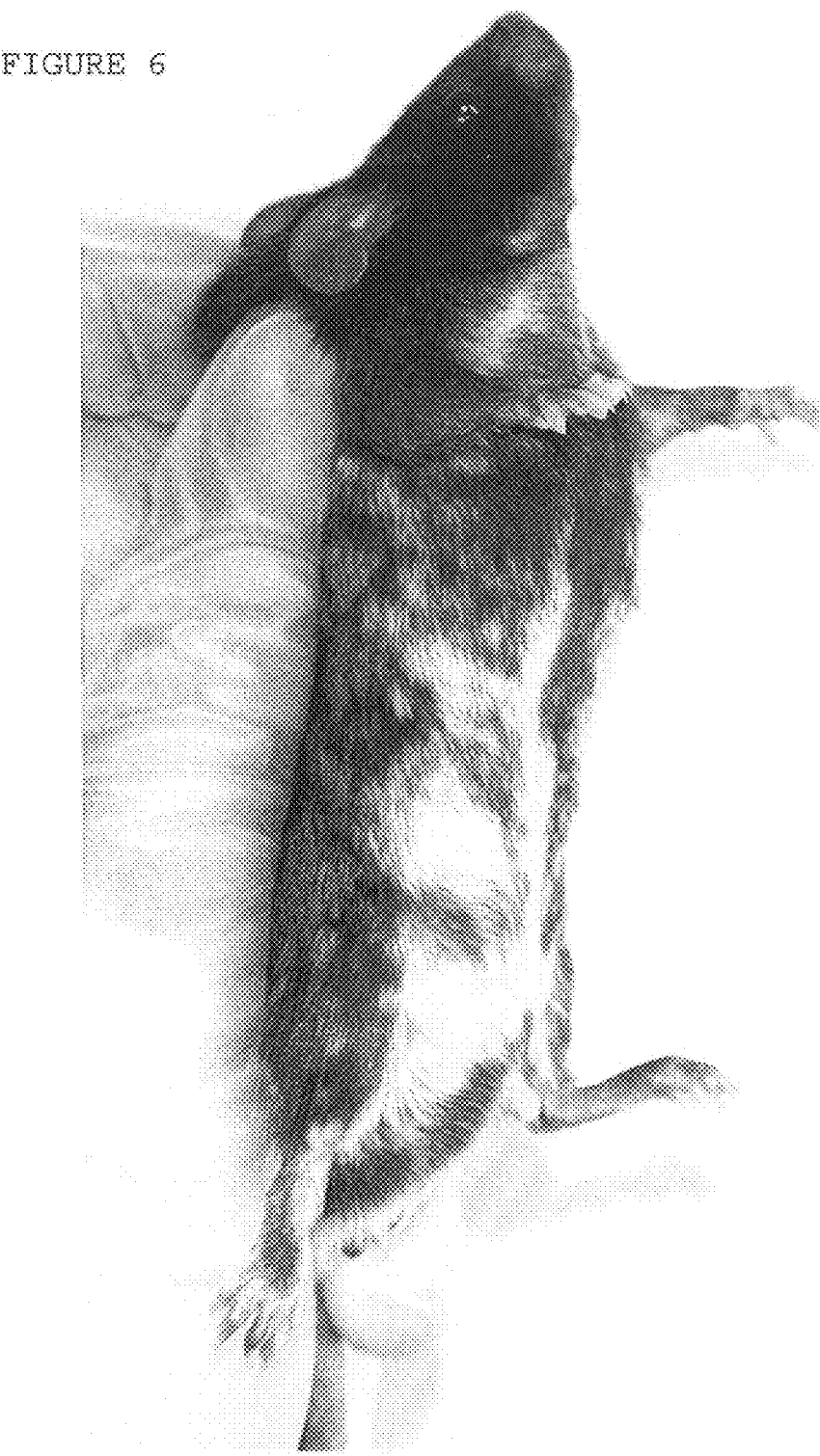
FIG. 6 is a photograph of a chimeric mouse derived from mouse embryonic stem cells cultured on laminin-511 for 3 months in absence of feeders and any differentiation inhibitors.

It has been found that when pluripotent mouse embryonic stem cells are cultured on plates coated with recombinant human laminin-5 (laminin-332) or laminin-10 (laminin-511) in the presence of mitogenic factor bFGF (10 ng/ml) and in the absence of any differentiation inhibitors, the cells proliferate and maintain their pluripotency for at least 140 days (23 passages) (FIG. 1a, FIG. 6). Expression of pluripotency markers, such as Oct4, TERT, Sox2, Nanog and UTF1 (FIG. 2, FIGS. 3a-3d, FIG. 4), and the proliferation rate (FIG. 1a), also remained stable. Furthermore, it was noted that the adhesion of embryonic cells to laminin-5 or laminin-10 molecules correlated with ability of the latter to sustain embryonic cells cell self-renewal (FIGS. 5a-5c).

Figure 1B:
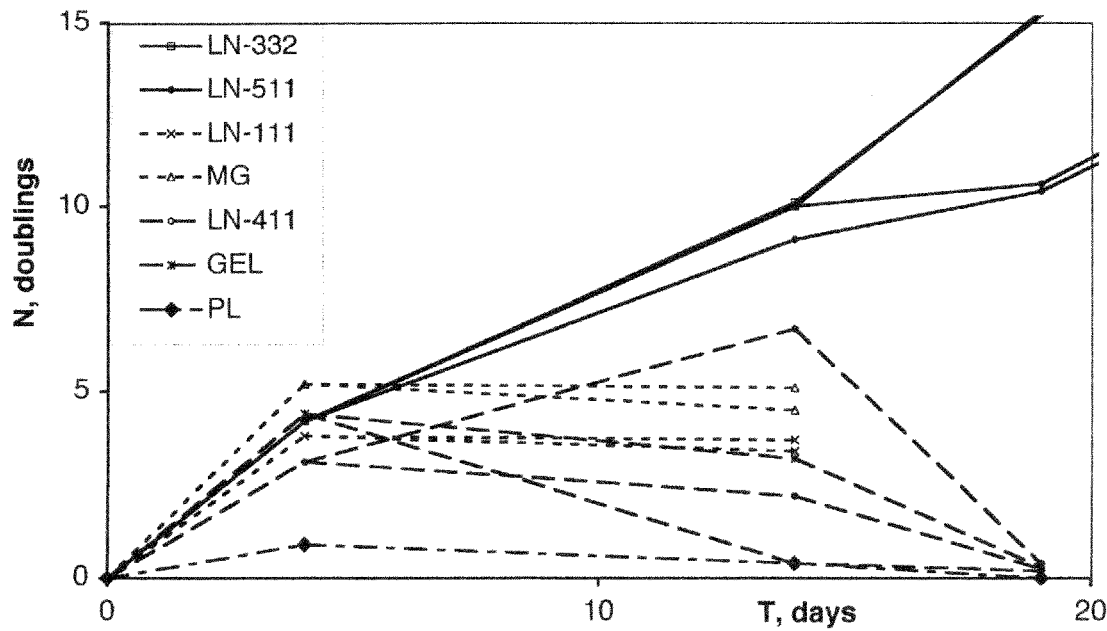
FIG. 1b is a graph showing magnification of days 1-20 in FIG. 1a, showing that the cells proliferated to a certain limit on LN-111, LN-411, Matrigel™ and gelatin, but proliferation ceased within 1-2 weeks. The cells attached poorly to poly-D-lysine.

In contrast, when the mouse embryonic stem cells were cultured under the same conditions on plates coated with mouse (EHS) laminin-1 (laminin-111), laminin-8 (laminin-411), Matrigel™ or gelatin, the pluripotent cells ceased proliferation after 1-2 weeks (FIG. 1b). They differentiated, or detached, or died. Additionally, cells cultured under these conditions on laminin-111 or Matrigel™ start to express differentiation markers such as collagen IV and brachyury and cease expression of pluripotency markers Oct4, Sox2, Nanog or UTF1 (FIG. 2, FIGS. 3a-3d).

Figure 7:
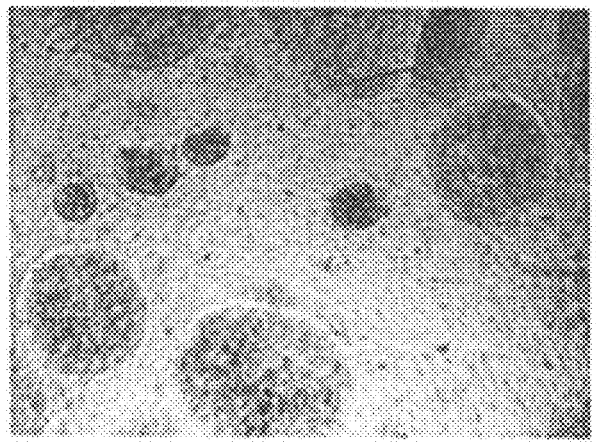
FIG. 7 is a microphotograph (phase contrast) of human embryonic stem cells on plates coated with recombinant laminin-10 (laminin-511) in a chemically defined medium after 105 days of feeder-free culturing.
Figure 8:
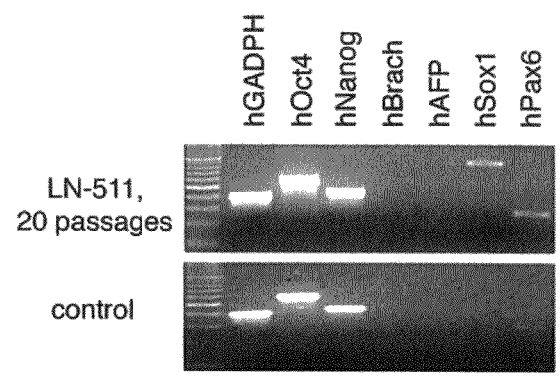
FIG. 8 is a photograph of RT-PCR showing the expression of pluripotency markers (Oct4, Nanog), internal control (GAPDH) and differentiation markers (alpha-fetoprotein, brachyury, Sox1 and Pax6) in human embryonic stem cells cultured on laminin-10 (laminin-511) in the chemically defined medium for 105 days (LN-511, 20 passages) and on human foreskin fibroblasts (control) in the conventional medium. Here, hGADPH, hOct4, hNanog, hBrach, hAFP, hSox1 and hPax6 stand for GAPDH, Oct4, Nanog, brachyury, alpha-fetoprotein, Sox1 and Pax6, respectively.
Figure 9:
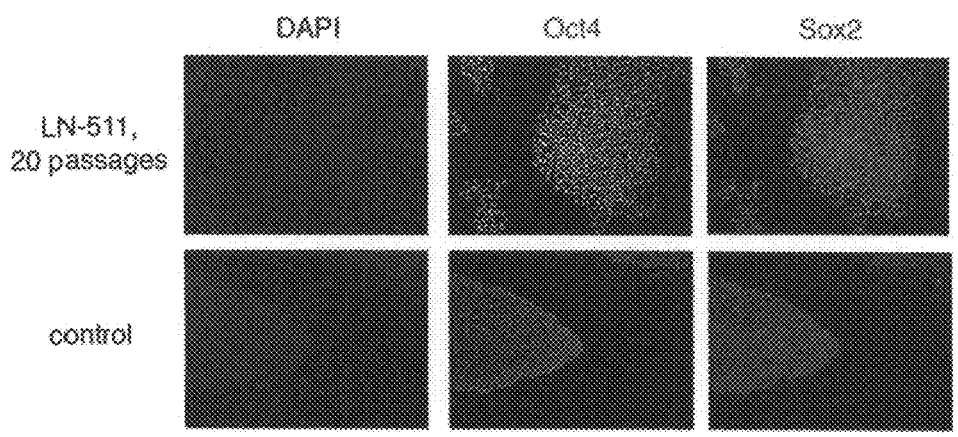
FIG. 9 contains a series of color microphotographs (immunofluorescence) demonstrating human embryonic stem cell self-renewal effect on laminins-511. After culturing on laminin-511 in the chemically defined media for 105 days (20 passages), human embryonic stem cells continue to express pluripotency markers Oct4 (green) and Sox2 (red) (LN-511, 20 passages). Human embryonic stem cells cultured on human foreskin fibroblasts in the conventional medium also express pluripotency markers Oct4 and Sox2 (control).

Also, it has been found that when pluripotent human embryonic stem cells are cultured on plates coated with recombinant human laminin-10 (laminin-511) in chemically defined medium, the cells proliferate and maintain their pluripotency for at least 105 days (20 passages) (FIGS. 7-9). Expression of pluripotency markers, such as Oct4, Sox2 and Nanog, and the proliferation rate, also remained stable.

The present disclosure will further be illustrated in the following non-limiting two sets of working examples, it being understood that these examples are intended to be illustrative only and that the disclosure is not intended to be limited to the materials, conditions, process parameters and the like recited herein. All proportions are by weight unless otherwise indicated.

Methods for First Set of Experiments

Cell Culture

Mouse embryonic stem cells (two lines were used: line GSI-1 derived from 129SvJ mice, provided by Uppsala University Transgenic Facility and line RW4) were cultured on extracellular matrix coatings in medium containing 80% Dulbecco's modified Eagle's medium (DMEM), containing GlutaMax-I and 4.5 g/liter glucose, 20% embryonic cells qualified fetal serum, 1% penicillin, 1% streptomycin, 10 mM Hepes buffer, 1 mM sodium pyruvate, non-essential aminoacids (all provided by Invitrogen), 0.1 mM beta-mercaptoethanol (Sigma) and 10 ng/ml beta fibroblast-growth factor (bFGF) (Chemicon) at 37° C., 5% $CO_2$. Embryonic cells were plated upon extracellular matrix coatings in initial density of 300 cells/$mm^2$. Cells were split once in 4-6 days by 0.05% trypsin-EDTA solution and plated at cell density of 180 cells/$mm^2$. Embryonic cells were cultured as two separate lines on each coating. Cells were counted during each passage using hematocytometer.

Human embryonic stem cells (two lines were used: HS420 and HS207, both kindly provided by Prof. Hovatta, Karolinska University Hospital Huddinge, Karolinska Institute, Sweden) and iPS cells derived from human fibroblasts were cultured on plates coated with recombinant laminin-10 (laminin-511) in the chemically defined medium, analog of mTeSR1. The medium was prepared as described in (Ludwig, T. E., Bergendahl, V., Levenstein, M. E., Yu, J., Probasco M. D. and Thomsom, J. A. (2006); Feeder-independent culture of human embryonic stem cells; Nat Methods 8, 637-646) with several exceptions. Firstly, recombinant human FGF basic (R@DSystems) was used instead of zbFGF and albumin from bovine serum (SIGMA-Aldrich, B4287) was used instead of BSA fraction V. Secondly, Insulin-Transferrin-Selenium Supplement (Invitrogen) added in already made medium was used as a source of the elements instead of the method described in the article. The human embryonic stem cells were passages in clumps at 4-6 days intervals by exposure to TrypLE™ Express (GIBCO). The cells were subjected to the enzyme for 2 minutes at room temperature, then washed 2 times with the medium, followed by gentle scraping to collect. Big clumps of the cells were broken by gentle pipetting and 1:3 passaged.

Control human embryonic stem cells were maintained on human foreskin fibroblasts in the conventional medium as described in (Inzunzaa, J., Gertow, K., Strömberg, M., A., Matilainen, E., Blennow, E., Skottman, H., Wolbank, S., Ährlund-Richter, L. and Hovatta, O. (2005); Derivation of Human Embryonic Stem Cell Lines in Serum Replacement Medium Using Postnatal Human Fibroblasts as Feeder Cells. Stem Cells 2005; 23:544-549). The cells were mechanically passaged by cutting the colony to eight pieces using a scalpel under the stereo microscope. Mechanical splitting was carried out at 6-day intervals. Nondifferentiated cells, as judged by morphology, were chosen for each further passage.

Plate Coating 96-well tissue cell culture plates (Sarstedt) were coated overnight at 4° C. by sterile solutions of extracellular matrix proteins: murine laminin-111 (Invitrogen), human recombinant laminin-332, human recombinant laminin-411 (Kortesmaa, J., Yurchenco, P., and Tryggvason, K. (2000); Recombinant laminin-8 (alpha(4)beta(1)gamma(1)). Production, purification, and interactions with integrins. J Biol Chem 275, 14853-14859, U.S. Pat. No. 6,638,907), human recombinant laminin-511 (Doi, M., Thyboll, J., Kortesmaa, J., Jansson, K., livanainen, A., Parvardeh, M., Timpl, R., Hedin, U., Swedenborg, J., and Tryggvason, K. (2002); Recombinant human laminin-10 (alpha5beta1gamma1); Production, purification, and migration-promoting activity on vascular endothelial cells. J Biol Chem 277, 12741-12748; U.S. Pat. No. 6,933,273), all in concentration 30 ug/ml (5 ug/$mm^2$), growth factor-depleted Matrigel™ (1:30) (BD Biosciences), bovine gelatin 1 mg/ml (Sigma), 0.1 mg/ml poly-D-lysine (Sigma).

Cell Adhesion Assays

Attachment assay was performed as described ([Extracellular Matrix Protocols, 2000). Briefly, MaxiSorp 96-well plates (Nunc) coated by extracellular matrix proteins as described above and blocked by 1% heat-denatured BSA solution. Undifferentiated embryonic cells were plated at cell density of 800 cell/$mm^2$ upon extracellular matrix-coated plates and were left to adhere for 1 hour at 37° C. Non-adherent cells were washed away, and adherent cells were fixed for 20 min by 5% glutaraldehyde, stained by 0.1% Crystal Violet.

RT-PCR:

Total RNA was isolated using Absolutely RNA Microprep Kit (Stratagene) according to the manufacturer's instructions from both mouse and human samples. cDNA was synthesized using 0.2 ug of total RNA in 20 ul reaction mixture, containing oligo(dT)12-18 primers and Superscript II reverse transcriptase (Invitrogen), according to the manufacturer's instructions). To compensate for variable cDNA yields, the amount of cDNA for each PCR reaction was calibrated by using expression level of the housekeeping gene GADPH as a standard. Amounts of cDNA yielding equivalent amount of GADPH PCR product (at 20 cycles, data not shown) were used for subsequent PCR reactions. cDNAs were amplified using primers from Table 1 for mouse samples and from Table 2 for human samples. All PCR reactions were run for 30 cycles (including those GADPH PCRs which are shown on pictures) and were performed in 20 μl under standard conditions using 1 U of Taq DNA Polimerase Recombinant (Invitrogen). The PCR products were analyzed on a 1.5% agarose gel containing ethidium bromide.

For each RNA sample, RT-PCR without reverse transcriptase was performed to confirm that no genomic DNA was isolated.

Immunofluorescence:

For immunofluorescence embryonic cells were fixed in 96-well plate wells by 4% paraformaldehyde, permeabilized by 0.1% Triton-X and blocked by 10% bovine fetal serum (Invitrogen) in 0.1% Tween-20 (Sigma) PBS for 1 hour. Incubation with primary antibody was performed for 1.5 hours at room temperature. Primary antibody against following mouse antigens were used: Oct4 (from BD Biosciences), Sox2, UTF, Nanog, Collagen IV (all from Millipore). Primary

TABLE 1

Primers for RT-PCR (mouse samples)

| Gene | Forward primer | Reverse primer | Product size (bp) | Ta, (C) |
|---|---|---|---|---|
| Oct-4 | AGGCCCGGAAGAGAAAGCGAACTA (SEQ ID NO: 1) | TGGGGGCAGAGGAAAGGATACAGC (SEQ ID NO: 2) | 266 | 64 |
| Sox-2 | GTGGAAACTTTTGTCCGAGACC (SEQ ID NO: 3) | TGGAGTGGGAGGAAGAGGTAAC (SEQ ID NO: 4) | 551 | 60 |
| TERT | CTGCGTGTGCGTGCTCTGGAC (SEQ ID NO: 5) | CACCTCAGCAAACAGCTTGTTCTC (SEQ ID NO: 6) | 498 | 64 |
| GADPH | GTGGAGATTGTTGCCATCAACGACC (SEQ ID NO: 7) | GGCTAAGCAGTTGGTGGTGCAGGA (SEQ ID NO: 8) | 393 | 64 |
| Vimentin | CAAGGGTGAGTAGAGAGTTCGGG (SEQ ID NO: 9) | TATAACACTGTTAGGAAAGAGGGTC (SEQ ID NO: 10) | 226 | 60 |
| Nestin | CGGCCCACGCATCCCCCATCC (SEQ ID NO: 11) | CAGCGGCCTTCCAATCTCTGTTCC (SEQ ID NO: 12) | 259 | 64 |
| Brachyury | GCTCATCGGAACAGCTCTCCAACC (SEQ ID NO: 13) | GGAGAACCAGAAGACGAGGACGTG (SEQ ID NO: 14) | 320 | 64 |
| AFP | GTTTTCTGAGGGATGAAACCTATGCC (SEQ ID NO: 15) | CGCCCAAAGCATCACGAGTTTTGG (SEQ ID NO: 16) | 285 | 64 |
| GATA4 | GGCCCCTCATTAAGCCTCAGCGC (SEQ ID NO: 17) | GCAGGACCTGCTGGCGTCTTAGAT (SEQ ID NO: 18) | 250 | 64 |

TABLE 2

Primers for RT-PCR (human samples)

| Gene | Forward primer | Reverse primer | Product size (bp) | Ta, (C) |
|---|---|---|---|---|
| Oct-4 | CGACCATCTGCCGCTTTGAG (SEQ ID NO: 19) | CCCCCTGTCCCCCATTCCTA (SEQ ID NO: 20) | 573 | 61 |
| Nanog | AGCATCCGACTGTAAAGAATCTTCAC (SEQ ID NO: 21) | CGGCCAGTTGTTTTTCTGCCACCT (SEQ ID NO: 22) | 433 | 61 |
| GADPH | GAAGGTGAAGGTCGGAGTCA (SEQ ID NO: 23) | TTCACACCCATGACGAACAT (SEQ ID NO: 24) | 402 | 59 |
| Pax6 | AACAGACACAGCCCTCACAAAC (SEQ ID NO: 25) | CGGGAACTTGAACTGGAACTGAC (SEQ ID NO: 26) | 275 | 61 |
| AFP | CTTTGGGCTGCTCGCTATGA (SEQ ID NO: 27) | TGGCTTGGAAAGTTCGGGTC (SEQ ID NO: 28) | 175 | 59 |
| Brachyury | GAAGGTGGATCTCAGGTAGC (SEQ ID NO: 29) | CATCTCATTGGTGAGCTCCTT (SEQ ID NO: 30) | 251 | 59 |
| Sox1 | CTCACTTTCCTCCGCGTTGCTTCC (SEQ ID NO: 31) | TGCCCTGGTCTTTGTCCTTCATCC (SEQ ID NO: 32) | 849 | 61 | antibody against following human antigens were used: Oct4 and Sox2 (both from R@DSystems). Incubation with secondary antibody (Alexa-488- and Alexa 546-labeled, Molecular probes) with DAPI (Molecular probes) was performed for 40 min. Between incubations specimens were washed with 0.1% Tween-20 in PBS three to five times, 10 min for each wash. Specimens were preserved in fluorescence mounting medium (Dako) and observed under fluorescent microscope (Leica).

Chimeric Mice:

After culturing for 95 days (17 passages) on laminin-511 and on laminin-332 mouse embryonic stem cells were expanded on mouse embryonic fibroblasts in presence of LIF and injected into C57BI mice blastocysts (procedure was performed in Karolinska Center for Transgene Technologies, Karolinska institute, Stockholm). Ethical permission #246/05 issued in Sep. 29, 2005 to Karl Tryggvason by the local ethical committee for experimental animal research.

Results for First Set of Experiments

A. Mouse Embryonic Stem Cells Cultured on Laminins-511 or -332 Proliferate and Remain Pluripotent in Absence of Feeders or LIF or any other Differentiation Inhibitors On laminin-511 and on laminin-332, mouse embryonic stem cells were found to remain pluripotent in absence of LIF or any other differentiation inhibitor for at least 140 days. See FIG. 1.

Proliferation: Proliferation rate of mouse embryonic stem cells cultured on Laminin-332 and -511 in absence of LIF/MEFs remained stable and same (high) during the whole duration of experiment. See FIG. 1a, b. From day 40 to day 80 doubling time equals 1.2 days.

RT-PCR markers: Pluripotency markers Sox2, Oct4 and proliferation marker Tert were expressed at same extent by mouse embryonic stem cells cultured on laminins-332 and-551 in absence of LIF for 145 days, as pluripotent embryonic stem cells cultured on LIF. See FIG. 2.

Immunofluorescence: The embryonic stem cells expressed pluripotency markers like Oct4, Sox2, UTF1 and Nanog at same extent as embryonic stem cells grown in presence of LIF. See FIG. 3a, b, c, d.

Morphology: Morphology of embryonic stem cells cultured on Laminin-332 and -511 differed significantly from embryonic stem cells cultured on MEFs or gelatin in presence of LIF. Embryonic stem cells cultured on MEFs or gelatine in presence of LIF formed dense clusters with sharp, defined borders. However, embryonic stem cells cultured on laminin-332 and -511 first spread over extracellular matrix coating forming monolayer, and only after that start forming layers. Nonetheless, expression of pluripotency markers Oct4 and Sox2 is not reduced. See FIG. 4.

In vivo (chimeric mice): mouse embryonic stem cells (line GSI-1) after 95 days (17 passages) of culturing on laminin-332 and of laminin-511 in absence of feeder cells or LIF or any other differentiation inhibitors were able to form chimeric mice. To verify that the mouse embryonic stem cells cultured on Laminin-511 or Laminin-332 in absence of feeder cells or differentiation inhibitors were pluripotent, cells maintained for 95 days (17 passages) were injected into mouse blastocysts that were subsequently implanted into pseudopregnant mice. This led to the generation of chimeric mice (FIG. 6) demonstrating that the cells were indeed pluripotent. Mouse embryonic stem cells (line RW4) also generated chimeric mice after 11 passages on laminin-511 or laminin-332 in absence of feeder cells or differentiation inhibitors.

B. Adhesion Correlates with Mouse Embryonic Stem Self-Renewal

It has been found that the ability of certain extracellular matrix components to support mouse embryonic stem cells self-renewal correlates with adhesion. Undifferentiated embryonic stem cells adhere strongly to laminin-332 and laminin-511 (FIGS. 5a and 5c). Average surface area of adherent embryonic stem cells on those laminins is 2.7 times higher than that of weakly attached embryonic stem cells (FIG. 5b). Adhesion of embryonic stem cells to laminin-111, Matrigel™, gelatin was not strong. Weak or no adhesion of embryonic stem cells to laminin-411, poly-D-lysine was observed. Student's two-tailed test reveals that difference between adhesion and surface area for laminin-511 and laminin-332 is statistically different from all other coatings (p-value below 5%).

C. Human Embryonic Stem Cells and Induced Pluripotent Stem Cells Cultured on Laminins-511 Proliferate and Remain Pluripotent in Chemically Defined Medium in Absence of Feeders On laminin-511, human embryonic stem cells were found to remain pluripotent in chemically defined medium for at least 105 days (20 passages) and iPS cells maintained pluripotency for at least five passages.

Morphology: Morphology of human embryonic stem cells cultured on Laminin-511 was very similar to that found for human embryonic stem cells cultured on Matrigel™ (Bendall, S., C., Stewart, M., H., Menendez, P., George, D., Vijayaragavan, K., Werbowetski-Ogilvie, T., Ramos-Mejia, V., Rouleau, A., Yang, J., Bossé, M., Lajoie, G. and Bhatia, M. (2007); IGF and FGF cooperatively establish the regulatory stem cell niche of pluripotent human cells in vitro. Nature, 2007 Aug. 30; 448(7157):1015-21.) or extracellular-matrix-coated plates (Klimanskaya, I., Chung, Y., Meisner, L., Johnson, J., West, M., D. and Lanza, R. (2005); Human embryonic stem cells derived without feeder cells. Lancet. 2005 May 7-13; 365(9471):1601-1603). See FIG. 7. But, unlike the two coatings mentioned above, recombinant human laminin-511 can be produced according to FDA requirements as a xeno-free, defined and nonimmunogenic compound and subsequently used in clinic.

RT-PCR markers: Pluripotency markers Oct4 and Nanog were expressed at same extent by human embryonic stem cells cultured on laminins-551 in the chemically defined medium for 105 days, as pluripotent embryonic stem cells cultured on human fibroblast foreskin in the conventional medium. See FIG. 8.

Immunofluorescence: Human embryonic stem cells expressed pluripotency markers like Oct4 and Sox2 at same extent as embryonic stem cells grown in conventional environment. See FIG. 9.

Summary of Second Set of Experiments

Specific laminin isoforms were tested for their ability to serve as substrata for maintaining mouse embryonic stem (ES) cells pluripotent in vitro in the absence of leukemia inhibitory factor (LIF) or any other differentiation inhibitors or feeder cells. Recombinant human laminin-511 alone (i.e. in the absence of differentiation inhibitors) was sufficient to enable self-renewal of mouse embryonic stem cells for up to 169 days (5 months, 31 passages). Cells cultured on laminin-511 maintained expression of pluripotency markers such as Oct4, Sox2, Tert, UTF1 and Nanog during the entire period, and cells cultured for 95 days (17 passages) were used to generate germline-competent chimeric mice. Laminin-332 enabled embryonic stem cell proliferation, but not pluripotency. In contrast, under the same conditions laminin-111, Matrigel, and gelatin substrates caused rapid differentiation, while laminin-411 and poly-D-lysine did not support survival. Embryonic stem cells form a thin monolayer on LN-511 that strikingly differs from typical dense cluster embryonic stem cell morphology. However, expression of pluripotency markers is not affected by morphological changes. The effect was achieved at low embryonic stem cell density (<200 cell/mm2). Ability of LN-511 and LN-332 to support embryonic stem cell proliferation correlated with increased cell contact area with those adhesive substrata. Embryonic stem cells interact with LN-511 via β1-integrins, mostly α6β1 and αVβ1.

These results demonstrated that certain extracellular matrix molecules can support embryonic stem cell self-renewal in the absence of differentiation inhibitors and at low cell density. The results suggest that recombinant laminin isoforms can provide a basis for defined surface coating systems for feeder-free maintenance of undifferentiated mammalian embryonic stem cells in vitro.

Materials and Methods

Cell Culture

Mouse embryonic stem cells (line GSI-1 derived from 129SvJ mice and line RW4) were cultured on extracellular matrix coatings in medium containing 80% Dulbecco's modified Eagle's medium (DMEM) supplemented by GlutaMax I and 4.5 g/liter glucose, 20% embryonic stem qualified fetal serum, 0.5% penicillin, 0.5% streptomycin, 10 mM Hepes buffer, 1 mM sodium pyruvate, 1% non-essential aminoacids (all provided by Invitrogen), 0.1 mM beta-mercaptoethanol (Sigma) and 10 ng/ml beta fibroblast-growth factor (bFGF) (Chemicon) at 37° C., 5% $CO_2$. Embryonic stem cells were plated upon extracellular matrix coatings at initial density of 300 cells/mm². Cells were split once in 4-6 days by 0.05% trypsin-EDTA solution and were plated at cell density of 180 cells/mm². Embryonic stem cells were cultured as two independent controls on each coating. Cells were counted after each passage using hematocytometer.

96-well tissue cell culture plates were coated overnight at 4° C. by seven different sterile solutions of extracellular matrix proteins: mouse LN-111 (Invitrogen), human recombinant LN-332, human recombinant LN-411, human recombinant LN-511, growth factor-reduced Matrigel™ diluted (1:30) (BD Biosciences), bovine gelatin 1 mg/ml (Sigma), and poly-D-lysine 0.1 mg/ml (Sigma). The four laminin-containing solutions had a concentration of 30 µg/ml (5 µg/cm²). The resulting cell culture plates had a substratum containing the extracellular matrix proteins, to which the stem cells and medium were subsequently added.

Antibody

To study pluripotency or differentiation status of embryonic stem cells primary antibodies against the following antigens were used: Sox2, Nanog, UTF, Collagen IV (all from Millipore) and Oct4 (Oct3/4 from BD Biosciences). To study integrin receptor expression and involvement in interaction with LN-511 in mouse embryonic stem cells, primary antibodies against the following subunits were used: α2, α2β1, α3, α4, α5β1, α6, αV, αVβ6, β1, β2, β4 from Chemicon; β1 from R&D Systems; α3, β1, β1 (function-blocking), β3 (function-blocking) from BD Biosciences and αV, β1, β3 (all function-blocking) from BioLegend. Immunoglobulins derived from respective species (Chemicon, BioLegend) were used as negative control. Secondary antibodies for immunofluorescence staining, anti-Mouse, Rat, Goat, Rabbit (Alexa-350, Alexa-488 and Alexa-546 labeled) were from Molecular Probes. HRP-conjugated anti-Mouse and anti-Rabbit secondary antibody used for Western blots were from GE Healthcare.

Immunofluorescence

For immunofluorescence embryonic stem cells were fixed in 96-well plate wells by 4% paraformaldehyde, permeabilized by 0.1% Triton-X and blocked by 10% bovine fetal serum (Invitrogen) in phosphate-saline buffer (PBS) containing 0.1% Tween-20 (Sigma) for 1 hour. Incubation with primary antibody was performed for 1.5 hours at room temperature. Incubation with secondary antibody and DAPI (Molecular Probes) was performed for 40 minutes. Between incubations specimens were washed with 0.1% Tween-20 in PBS buffer three to five times, were preserved in fluorescence mounting medium (Dako) and observed under fluorescent microscope (Leica).

RT-PCR:

Total RNA was isolated using Absolutely RNA Microprep Kit (Stratagene) according to the manufacturer's instructions. cDNA was synthesized using 0.2 µg of total RNA in 20 µl reaction mixture, containing oligo(dT) 12-18 primers and Superscript II reverse transcriptase (Invitrogen), according to the manufacturer's instructions. To compensate for variable cDNA yields, the amount of cDNA for each PCR reaction was calibrated by using expression level of the housekeeping gene GADPH as a standard. Amounts of cDNA yielding equivalent amount of GADPH PCR product (at 20 cycles, data not shown) were used for subsequent PCR reactions. cDNAs were amplified using primers from Table 1. All PCR reactions were run for 30 cycles (including those GADPH PCRs which are shown on pictures) and were performed in 20 µl under standard conditions using 1 U of Taq DNA Polymerase Recombinant (Invitrogen). The PCR products were analyzed on a 1.5% agarose gel containing ethidium bromide. For each RNA sample, RT-PCR without reverse transcriptase was performed to confirm that no genomic DNA were isolated.

Western Blot and Densitometry Analysis:

After culturing on different extracellular matrix coatings, as described above, mouse embryonic stem cells were collected, counted and pelleted by centrifugation, mixed with non-reduced SDS-PAGE sample buffer to equal concentration of 2000 cells/µl and sonicated 5 times×15 seconds. Gradient 4-12% gels were used for SDS electrophoresis and the proteins were transferred to PVDF membranes. Membranes were blocked by 5% milk solution in PBS-0.1% Tween buffer for 2 hours. Primary antibody against Oct-3/4 (1:300) and Sox2 (1:1000) in 5% milk solution in PBS-0.1% Tween buffer were incubated with the membranes overnight at +4° C. After being washed 4 times, HRP-conjugated secondary antibodies 5% milk solution in PBS-0.1% Tween buffer (dilution 1:1000) were incubated with the membranes for 40 min at room temperature and washed 5 times with PBS. Chemoluminescent HRP-substrate from Amersham Biosciences was used for visualization. Films were scanned at 600 dpi and analyzed by the ChemImager5500 program (1D-Multi Line densitometry mode). Mouse embryonic stem cells cultured in the presence of LIF were used as positive control. Error bars show range.

Chimeric Mice and Germ Line Transmission

After culturing for 95 days (17 passages) on laminin-332 and on laminin-511 embryonic stem cells of GSI-1 line were injected into C57BI mice blastocysts (procedure was performed in Karolinska Center for Transgene Technologies, Karolinska institute, Stockholm). Embryonic stem cells of RW4 line were injected after 45-50 days (11-15 passages) in same way. All male and some female chimeras were tested for germ line transmission by breeding with CBL57 mice. Ethical permission was obtained from the local ethical committee for experimental animal research.

Cell Adhesion Assay

Attachment assay was performed. Briefly, MaxiSorp 96-well plates (Nunc) coated by extracellular matrix proteins as described above and blocked by 1% heat-denatured BSA solution. Undifferentiated embryonic stem cells were plated at cell density of 800 cell/mm$^2$ upon extracellular matrix-coated plates and were left to adhere for 1 hour at 37° C. Non-adherent cells were washed away, and adherent cells were fixed for 20 min by 5% glutaraldehyde, washed and stained by 0.1% Crystal Violet. After 1 hour Crystal Violet was extracted from cells by 10% acetic acid and quantified by measuring optical density at 570 nm. Error bars show standard deviation (STD, n=3).

Cell Contact Area Measurement for Adhesion/Blocking Experiments

For measuring cell contact area undifferentiated embryonic stem cells were plated (150 cells/mm$^2$) and then treated, fixed and stained as described above. Photos of 10-20 random fields were taken and the cell contact area of 40-150 cells was measured using the Velocity imaging software (Improvision). Error bars show standard error (SEM).

Adhesion-blocking Assay Using Anti-integrin Antibody.

Adhesion-blocking assays were performed as described previously. Briefly, plates were coated by LN-511 and blocked by 1% heat-denatured BSA solution. Embryonic stem cell suspension was incubated with function-blocking anti-integrin antibodies (concentration as recommended by supplier) for 30 minutes, plated on LN-511-coated plates and allowed to adhere for 1 hour at 37° C. Non-attached cells were removed and the remaining cells were fixed, stained and quantified as described above (Cell adhesion assay). Error bars show standard error (SEM).

Cell Attachment to Surface Coated by Anti-integrin Antibody Assay.

The assay was designed to identify integrin receptors that are expressed in sufficient amounts to retain cells attached to the surface coated by anti-integrin specific antibody. MaxiSorp 96-well plates (Nunc) were coated with purified anti-integrin antibodies in concentration of 10 µg/ml at +4° C. overnight and later washed and blocked by 1% heat-denatured BSA solution. Embryonic stem cells were plated on antibody-coated plates and allowed to adhere for 1 hour at 37° C. Non-attached cells were removed and remaining cells were fixed, stained and quantified as described above (Cell adhesion assay). Error bars show standard error (SEM).

Affymetrix Array

RNA was extracted from undifferentiated embryonic stem cells as described above and frozen to −80° C. Affymetrix array MOE 430 2.0 was performed by the core facility of the Karolinska Institute.

Sequence Similarity Analysis

Comparison of mouse and human laminin chains sequence similarity was performed using BLAST tool, available on the World Wide Web at pubmed.gov.

Statistics

Statistical significance was determined by Student's two-tailed t-test for unequal variences.

Results of Second Set of Experiments

To explore if specific laminin isoforms can either trigger differentiation or sustain self renewal, we cultured mouse embryonic stem cells in vitro without any feeder cells, or differentiation inhibitors, or differentiation inductors. We produced and purified recombinant human LN-332, LN-411 and LN-511 from culture media of HEK293 cells as described previously, and obtained commercially available mouse LN-111 (Invitrogen) isolated from the EHS sarcoma. Additionally, Matrigel™, gelatin and poly-D-lysine were used, for a total of seven different substrates.

As positive control for undifferentiated mouse embryonic stem cells in our experiments, we used embryonic stem cells cultured in the presence of differentiation inhibitor LIF on gelatin. This is the best documented conventional system for feeder-free culture of mouse embryonic stem cells that has successfully been used for decades.

LN-511 Enables Mouse Embryonic Stem Cell Self-renewal in Absence of Differentiation Inhibitors for at Least 169 Days.

Mouse embryonic stem cells cultured on LN-511 proliferated at a stable rate in absence of feeder cells or LIF for at least 169 days (31 passages), the average doubling time equaling 1.2 days. See generally FIGS. 1a and 1b.

Figure 10:
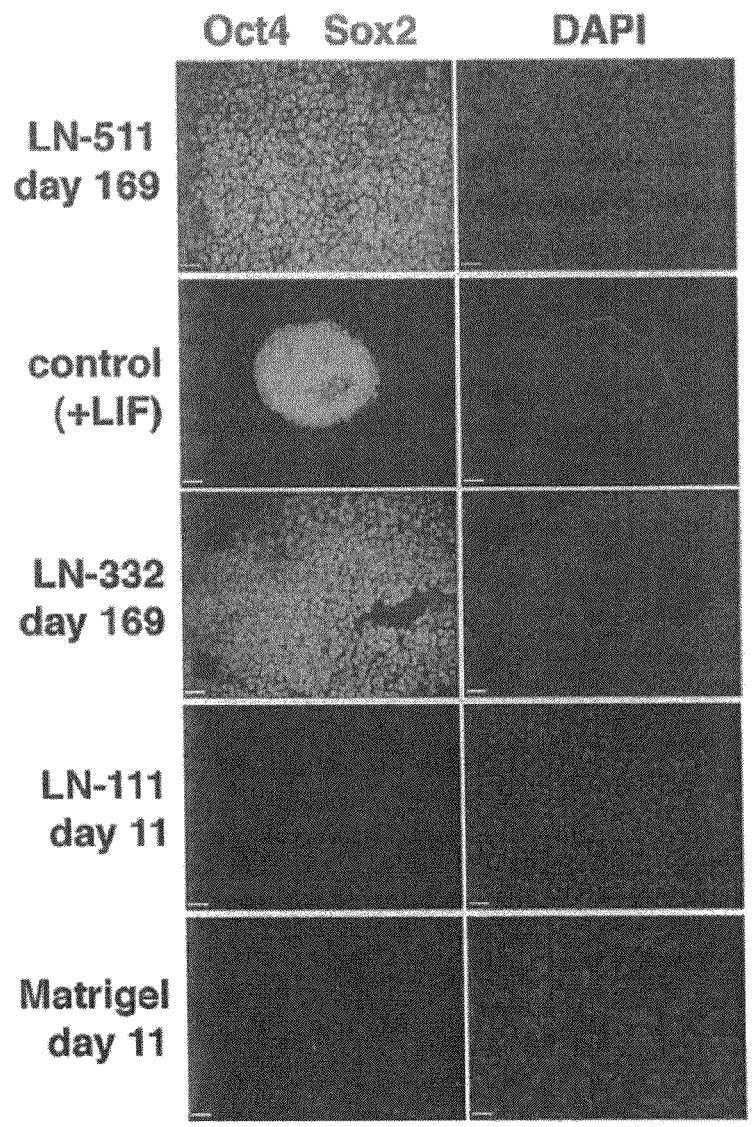
FIG. 10 is a set of photomicrographs of immunofluorescence staining against pluripotency markers Oct4 and Sox2. Embryonic stem cells cultured in presence of LIF (control+LIF) express pluripotency marker Oct4 and Sox2 (control). After culturing on laminin-332 or laminin-511 in absence of LIF or any other differentiation inhibitor for 169 days, embryonic stem cells continue to express Oct4 (green) and Sox2 (red). It is noteworthy that after culturing for only 11 days on laminin-111 or on Matrigel™, embryonic stem cells cease to express Oct 4 and Sox2. Magnification 40×. Bar size 27 μm.
Figure 11A:
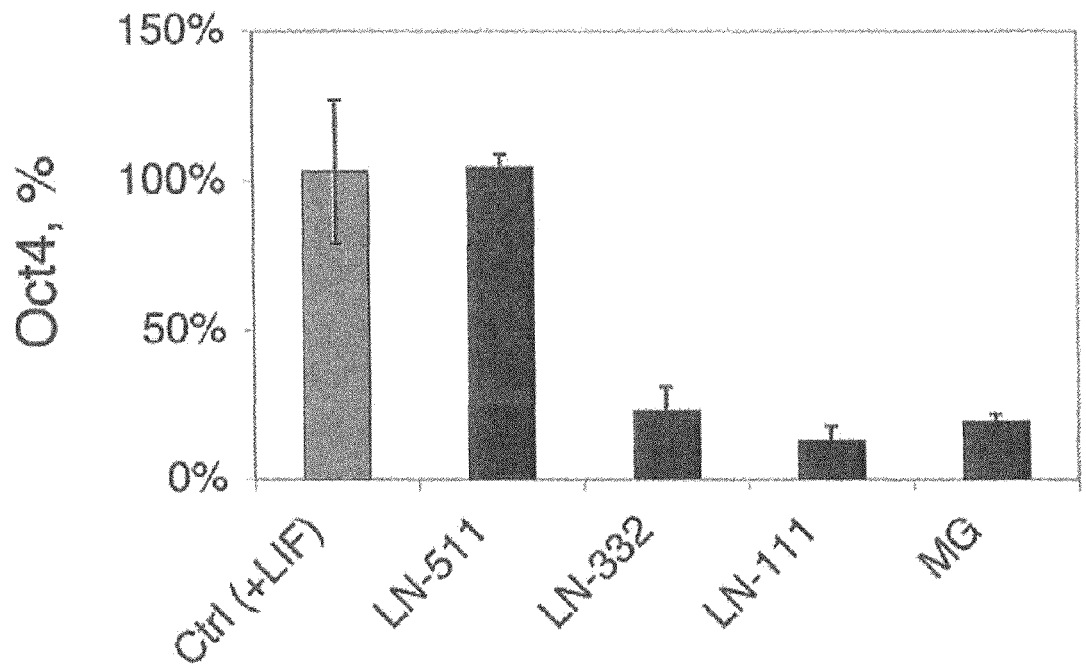
FIG. 11a is a graph showing the expression of pluripotency marker Oct4 in mouse embryonic stem cells, cultured on LN-511 (over 5 months), LN-332 (over 5 months), LN-111 (less than 20 days), or Matrigel™ (less than 20 days), measured by Western blot and quantified by densitometry. Expression was compared to positive control embryonic stem cells cultured with LIF. Error bars represent range.
Figure 11B:
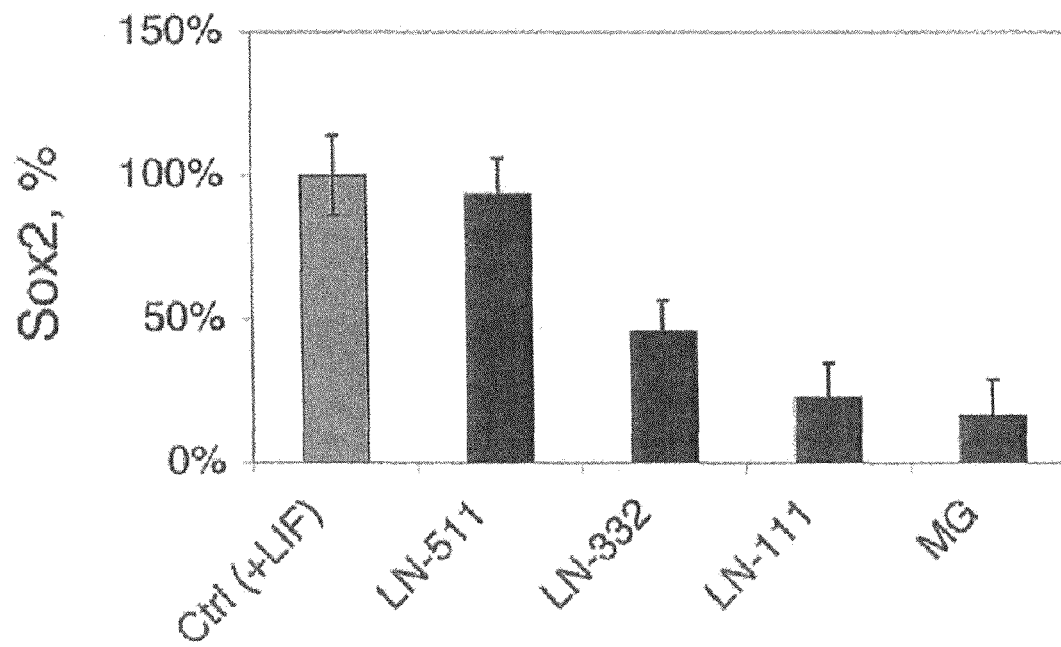
FIG. 11b is a graph showing the expression of pluripotency marker Sox2 in mouse embryonic stem cells, cultured on LN-511 (over 5 months), LN-332 (over 5 months), LN-111 (less than 20 days), or Matrigel™ (less than 20 days), measured by Western blot and quantified by densitometry. Expression was compared to positive control embryonic stem cells cultured with LIF. Error bars represent range.

Importantly, immunofluorescence, RT-PCR and quantitative Western blot analyses revealed that the embryonic stem cells expressed pluripotency markers, such as Sox2, Oct4, Tert, UTF1 and Nanog (see generally FIGS. 2, 10, 11a, 11b, 17, and 18). The pluripotency markers were expressed during the entire experiment to the same extent as control pluripotent embryonic stem cells cultured in presence of LIF. Expression of differentiation markers such as alpha-fetoprotein, brachyury, nestin and vimentin, was low or non-existent throughout the experiment (see FIG. 2). Levels of pluripotency markers Oct4 and Sox2 were measured using Western blot and quantified by densitometry (FIGS. 11a, 11b). Embryonic stem cells cultured on LN-511 for over 3 months maintained levels of those markers at the same level as the control (105% and 94% respectively, compared to positive control embryonic stem cells cultured in presence of LIF).

Figure 12A:
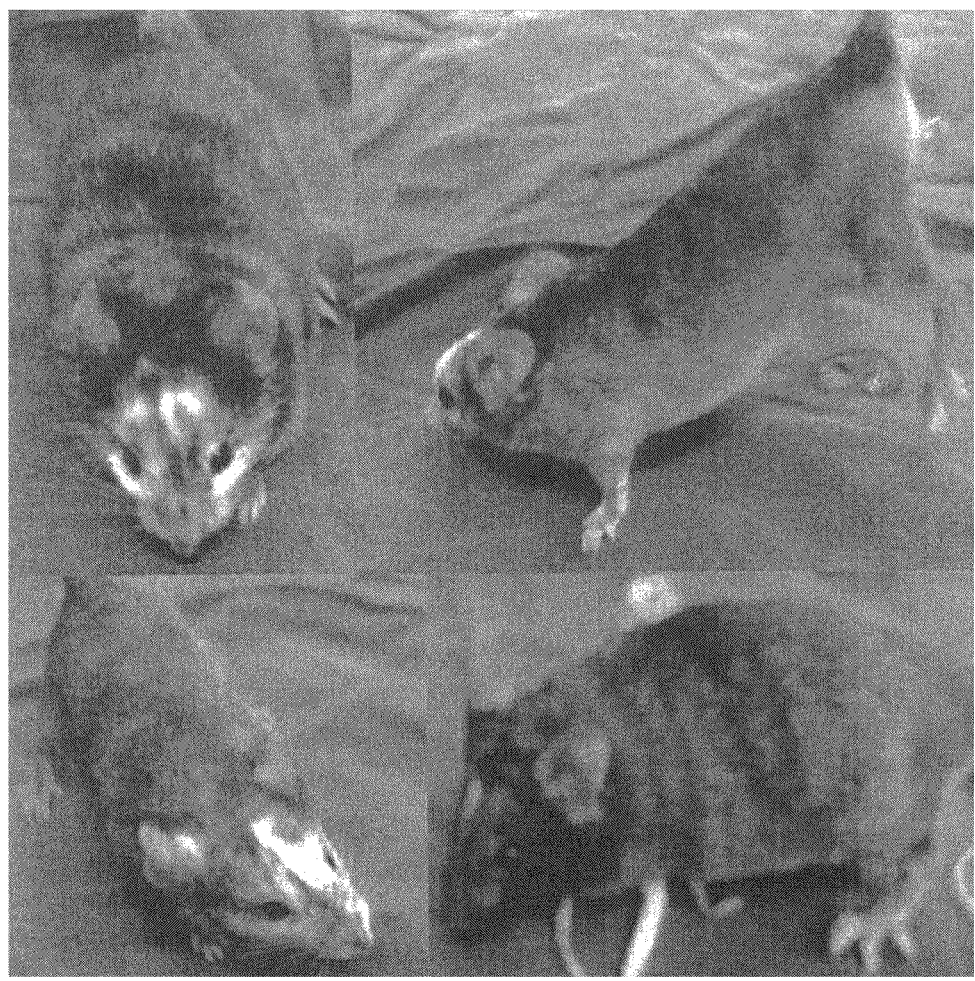
FIG. 12a shows chimeric mice generated from mouse embryonic stem cell line RW4 cultured for 45-50 days (11-15 passages) on LN-511.
Figure 12B:
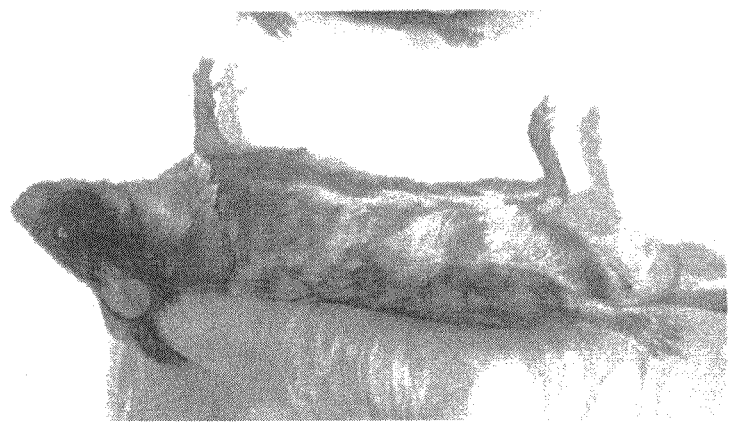
FIG. 12b shows a chimeric mouse generated from mouse embryonic stem cell line GSI-1 cultured for 95 days (17 passages) on LN-511.
Figure 12C:
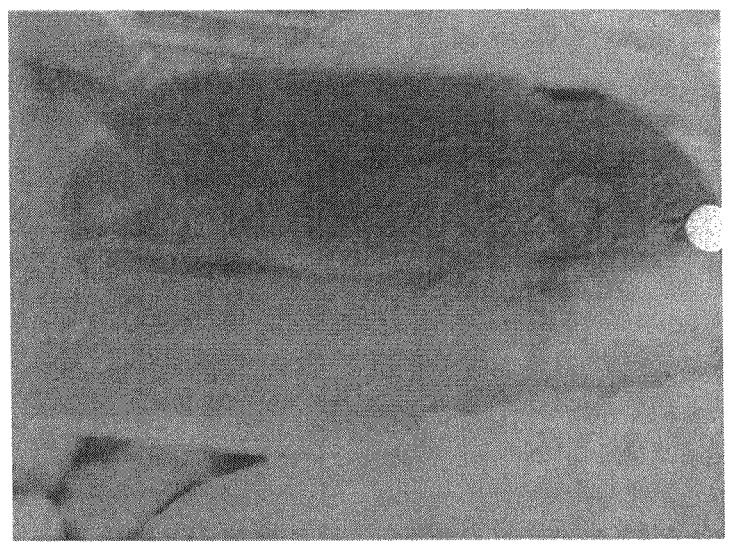
FIG. 12c shows a brown mouse obtained from breeding of a RW4 chimeric male and a CBL57 female mouse demonstrating germ line transmission.
Figure 13:
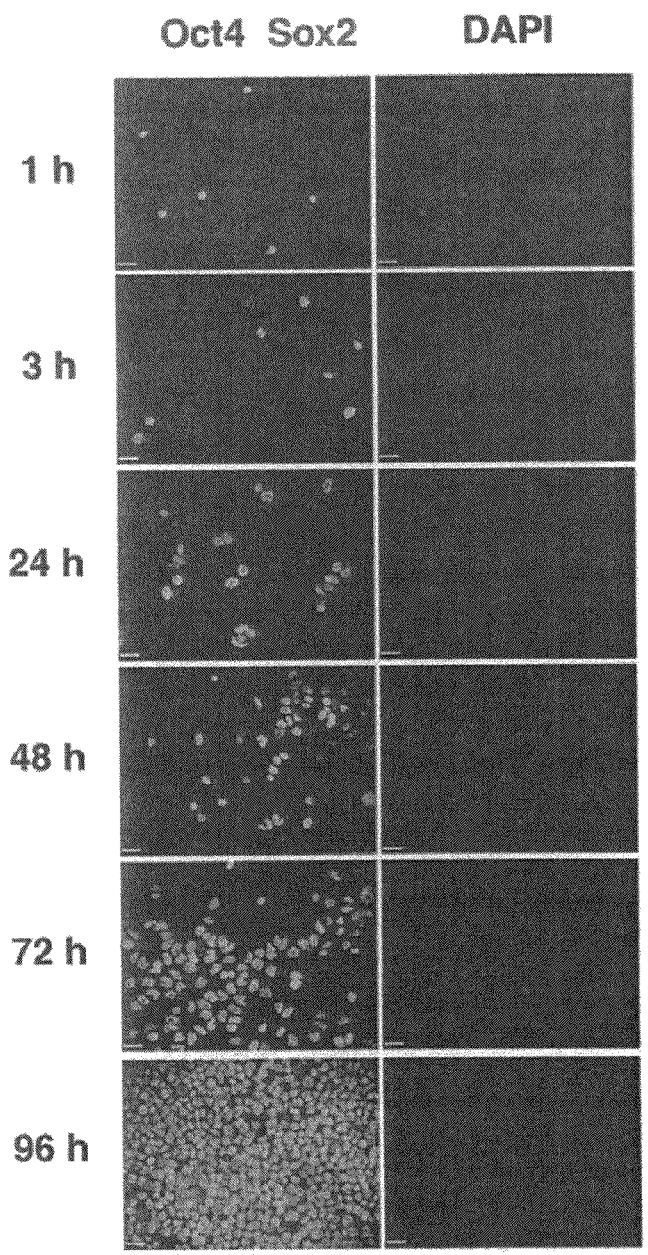
FIG. 13 is a series of color photomicrographs (Immunofluorescence (×40)) demonstrating the mechanism of mouse embryonic stem cell pluripotency maintenance when cultured on laminin-511 in absence of LIF or any other differentiation inhibitor. Embryonic stem cells cultured on laminin-511 in absence of differentiation inhibitors for 80 days, plated at cell density 180 cell/mm$^2$. Photomicrographs were taken in intervals: 1, 3, 24, 28, 72, and 96 hours, respectively. The cells adhered, proliferated and were studied for expression of Sox2 (red), Oct4 (green) and presence of DNA (DAPI, blue) at different time points. All cells expressed pluripotency markers and in most cases the cells did co-express Oct4 and Sox2 (yellow) as shown by merged images. Pluripotency marker Sox2 is expressed at the same level during the first 2 days. Embryonic stem cells are not in contact with each other, but only contact laminin-511.

To verify that the embryonic stem cells cultured on LN-511 were pluripotent, cells maintained for 95 days (17 passages) were injected into mouse blastocysts that were subsequently implanted into pseudopregnant mice. This led to the generation of chimeric mice (FIGS. 12a, 12b) and subsequently to germ line transmission (FIG. 12c) demonstrating that the cells were indeed pluripotent. Two different mouse embryonic stem cell lines (GSI-1 and RW4) were used to generate chimeric mice. The percentage of chimeras among the progeny and degree of chimerism for both lines did not differ from positive control embryonic stem cells cultured in presence of LIF, as shown in Table 3 below, which shows the efficiency of chimaera formation of mouse embryonic stem cell lines cultured on different coatings.

TABLE 3

| Culture | Pups, born | Chimaeras | % chimaeras | Degree of chimerism, % surface body area |
|---|---|---|---|---|
| RW4 cell line | | | | |
| Control (+LIF) | 17 | 12 | 71% | Strong (40-90% body area) |
| LN-511 | 20 | 11 | 55% | Strong (40-90% body area) |
| LN-511 | 27 | 11 | 41% | Strong (40-90% body area) |
| LN-511 | 10 | 9 | 90% | Strong (40-90% body area) |
| LN-332 | 14 | 0 | 0% | None |
| LN-332 | 14 | 0 | 0% | None |
| GSI-1 cell line | | | | |
| Control (+LIF) | 11 | 4 | 36% | Weak (0-25% body area) |
| LN-511 | 35 | 12 | 34% | Weak (0-25% body area) |
| LN-511 | N/a | >10 | N/a | Weak (0-25% body area) |
| LN-332 | N/a | — | — | — |
| LN-332 | N/a | >2 | | Very weak (0-5% body area) |

Mouse Embryonic Stem Cells Cultured on LN-332 Proliferate, but Do Not Maintain Pluripotency.

Mouse embryonic stem cells cultured on LN-332 proliferated for 169 days with similar high rate as on LN-511 (see FIGS. 1a, 1b) and expressed pluripotency markers (see FIGS. 2, 10, 11a, 11b). However, quantification of Western blot revealed that Oct4 and Sox2 levels declined to 23% and 46%, respectively, in comparison with the positive control. Notably, mouse embryonic stem cells cultured on LN-332 either formed weak chimeras (line GSI-1) or could not form any chimeras at all (line RW4). The results reveal a distinct difference between the effects of LN-511 and LN-332 on mouse embryonic stem cells. Apparently LN-332 could support cell proliferation, but not mouse embryonic stem cell self-renewal.

Mouse Embryonic Stem Cells Cultured on LN-111 or Matrigel™ Undergo Differentiation Within 2 Weeks, While LN-411 Does Not Support Embryonic Stem Cell Survival.

Figure 2:
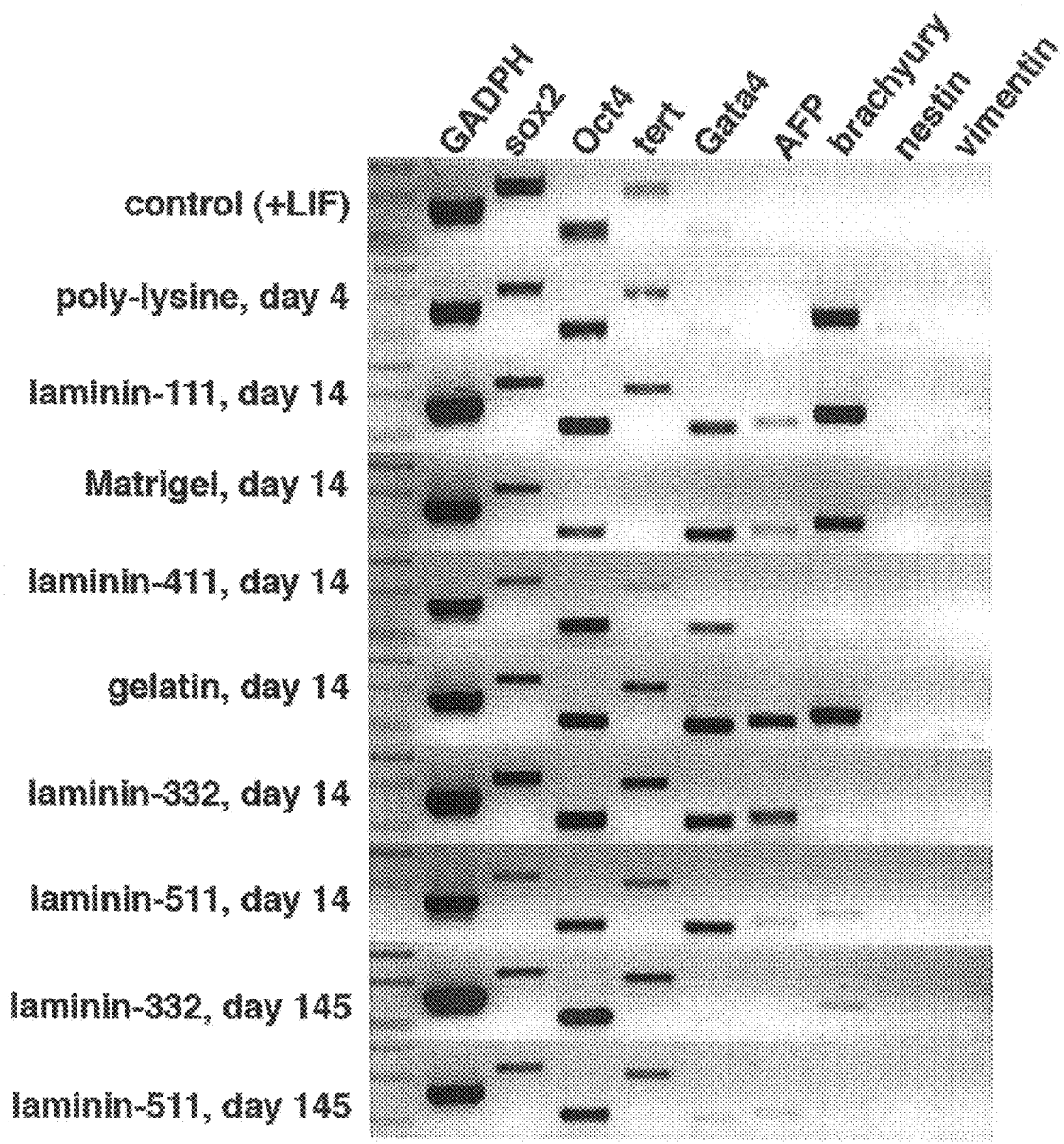
FIG. 2 is a photograph of RT-PCR showing the expression of pluripotency markers (Sox2, Oct4), proliferation marker (Tert) and differentiation markers (alpha-fetoprotein, brachyury, nestin and vimentin) in mouse embryonic stem cells cultured on laminins-111, -332, -411, -511, Matrigel™, gelatin and poly-D-lysine in absence on any differentiation factors or differentiation inhibitors for up to 145 days. Pluripotent mouse embryonic stem cells grown on LN-332 or LN-511 for 14 or 145 days maintained expression of pluripotency markers Sox2 and Oct4, but exhibited only low expression of differentiation markers such as brachyury and alpha-fetoprotein (AFP). Control pluripotent embryonic stem cells grown in the presence of LIF exhibited similar expression profile. In contrast, cells grown for 14 days on LN-111, Matrigel™ (MG) or gelatin (Gel) started to express brachyury and alpha-fetoprotein as a sign of differentiation. Cells grown on LN-411 did not differentiate, but they did not properly adhere or proliferate. The cells survived only a few days on poly-D-lysine (PL) but they differentiated already during that time.
Figure 3D:
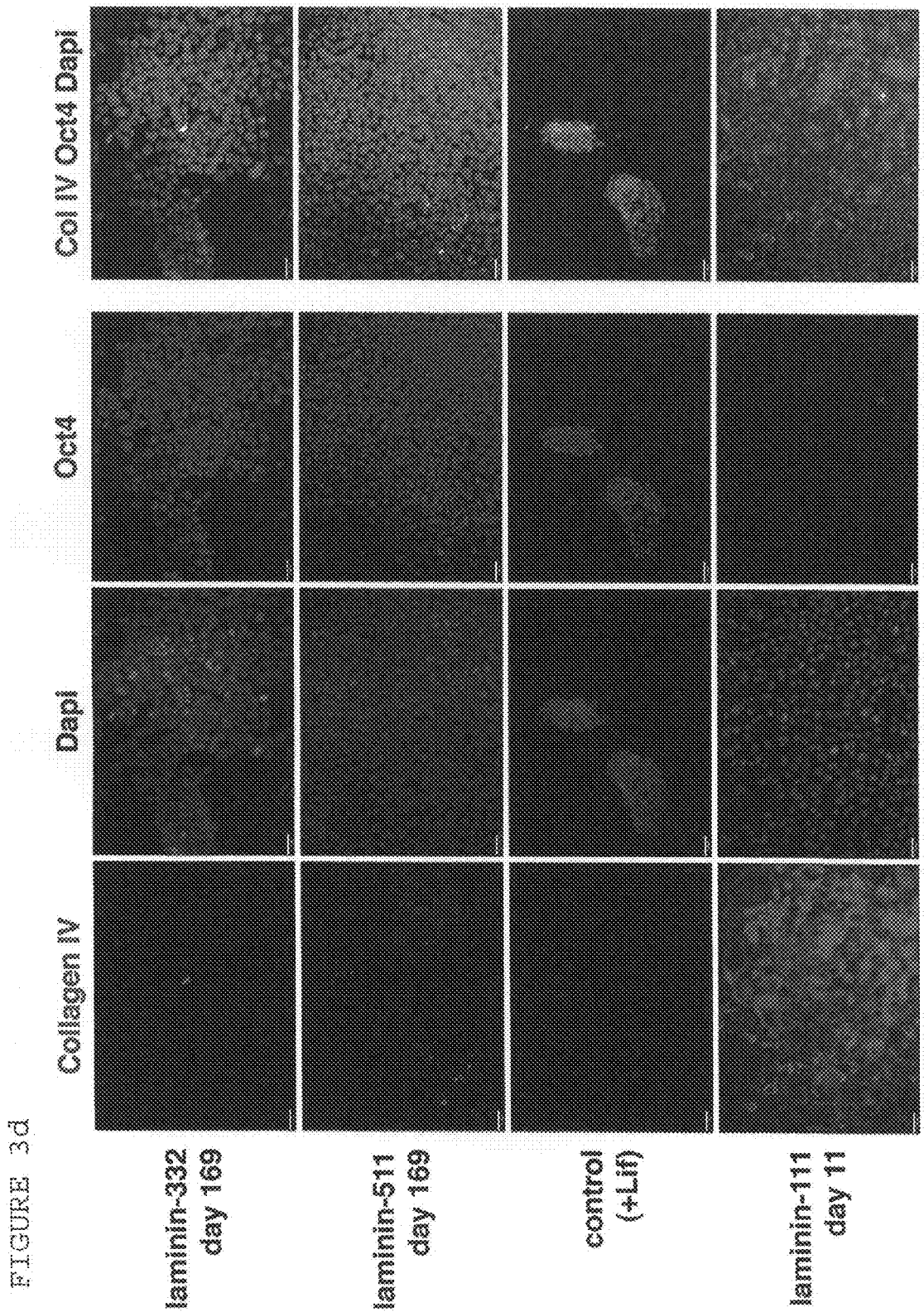
Figure 4:
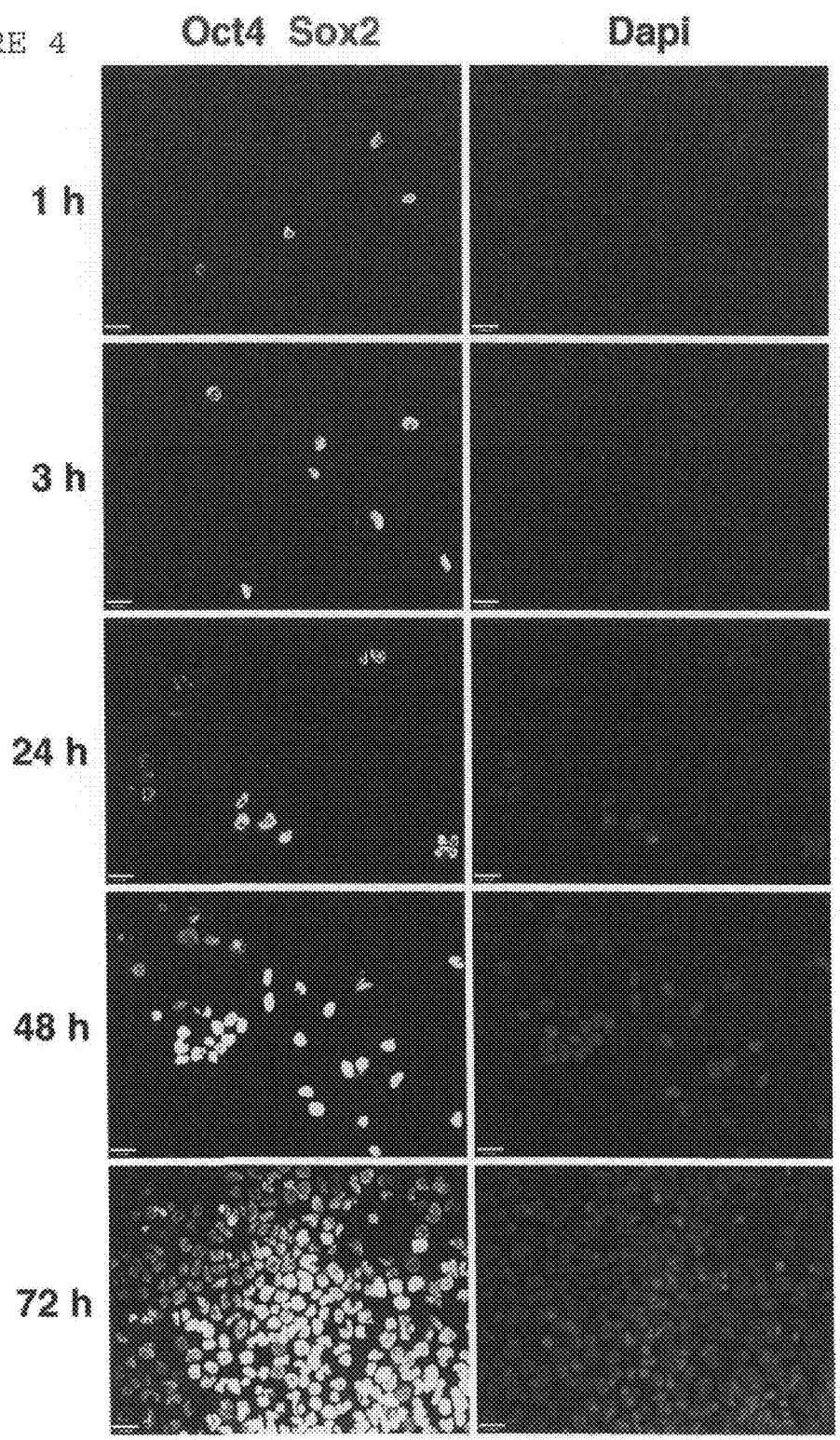
FIG. 4 is a series of color photomicrographs (Immunofluorescence (×40)) demonstrating the mechanism of mouse embryonic stem cell pluripotency maintenance when cultured on laminin-511 in absence of LIF or any other differentiation inhibitor. Embryonic stem cells cultured on laminin-511 in absence of differentiation inhibitors for 80 days, plated at cell density 180 cell/mm$^2$. Photomicrographs were taken in intervals: 1 hour, 3 hours, 1 day, 2 days, and 3 days. The cells adhered, proliferated and were studied for expression of Sox2 (red), Oct4 (green) and presence of DNA (DAPI, blue) at different time points. All cells expressed pluripotency markers and in most cases the cells did co-express Oct4 and Sox2 (yellow) as shown by merged images. Pluripotency marker Sox2 is expressed at the same level during the first 2 days. Embryonic stem cells are not in contact with each other, but only contact laminin-511.

In contrast to LN-511 and LN-332, cells cultured on LN-111 or Matrigel did not proliferate or self-renew in the absence of differentiation inhibitors. Within 4 days, proliferation ceased in absence of LIF (FIG. 1b), and after 11 days the cells formed cobblestone-like structures and started to express differentiation markers such as collagen IV (FIG. 3d) and brachyury (FIG. 2), but decreased expression of pluripotency markers Sox2, Oct4, Nanog and UTF1 (FIGS. 2, 10, 3d, 11a, 11b, 17, 18). Although proliferation had ceased, the differentiated cells remained viable for at least 25-30 days retaining cobblestone-like morphology. The embryonic stem cells did not survive on LN-411 or poly-D-lysine, due to low adhesion. When cultured on gelatin, the cells underwent spontaneous differentiation (FIG. 2). Differentiation markers such as alpha-fetoprotein and brachyury were strongly expressed, while nestin and vimentin exhibited lower expression levels.

All extracellular matrix coatings considered above, including laminin-111 and Matrigel™, were not able to sustain embryonic stem cell self-renewal or proliferation in the absence of differentiation inhibitors.

Contact with LN-511 is Sufficient to Maintain Pluripotency of Mouse Embryonic Stem Cells.

To study if contact with LN-511 is indeed the only factor sufficient for embryonic stem cells self-renewal, we monitored embryonic stem cell status for several days after re-plating them, as usual, at low cell density. LN-511 supported pluripotency of undifferentiated mouse embryonic stem cells even under low cell density conditions where the cells lack contacts with other cells, soluble differentiation inhibitors, or any other extracellular matrix proteins for at least 2 days (FIG. 10). Thus, expression of the pluripotency markers Sox2 and Oct4 remained stable and the cells proliferated rapidly and spread when placed upon LN-511. The results indicate that LN-511 is indeed a factor that can by itself transmit signals necessary and sufficient for sustaining self-renewal and promotion of rapid proliferation. Notably, embryonic stem cells, when cultured on other coatings, need not only soluble differentiation inhibitors like LIF, but also constant multiple cell contacts with neighbor cells for pluripotency maintenance.

Strong Adhesion to LN-511 Results in Spread Monolayer Morphology of Undifferentiated Embryonic Stem Cells.

Figure 15A:
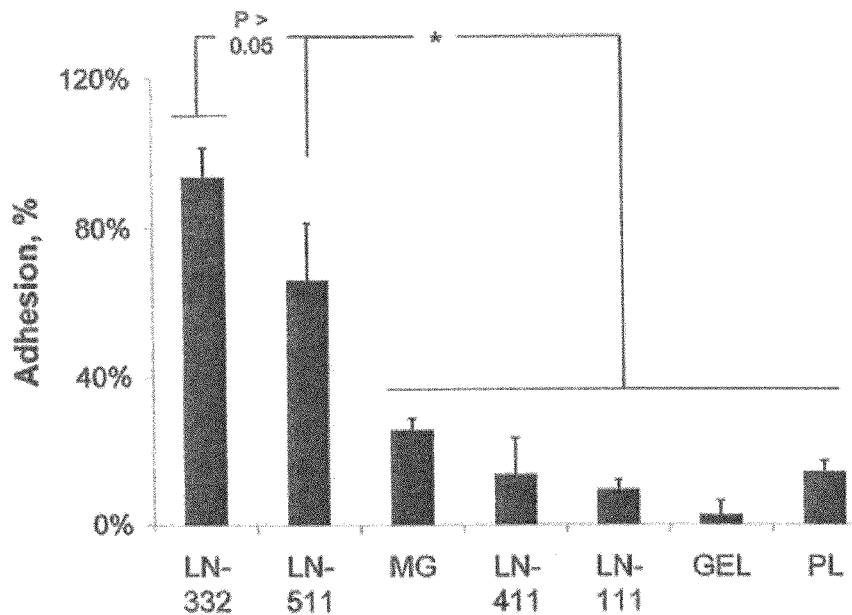
FIG. 15a is a graph showing the adhesion of mouse embryonic stem cells to different coating surfaces: laminins (LN), Matrigel™ (MG), gelatin (GEL), and poly-D-lysine (PL). Values are shown as average percentage of cells that attached. Error bars show standard deviation (STD, n=3). Statistical significance calculated by the Student t-test is shown as: (*) for P<0.05.
Figure 15B:
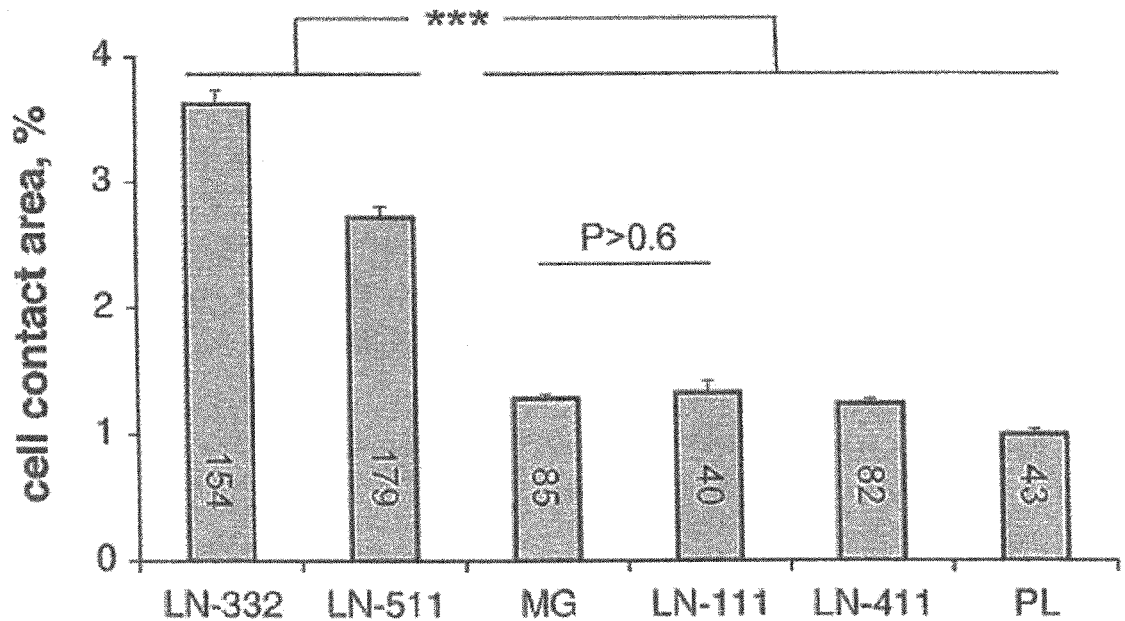
FIG. 15b is a graph showing the contact area of mouse embryonic stem cells to different coating surfaces. Values are shown as average relative cell contact area (compared to non-spread embryonic stem cells, %). Error bars show standard error (SEM), the number inside each bar shows number of independent measurements (n from 40 to 179). Statistical significance calculated by the Student t-test is shown as: (***) for P<0.001.

Interestingly, proliferation of the mouse embryonic stem cells promoted by certain laminin isoforms correlated with the adhesion to those isoforms (LN-511 and LN-332) (see FIGS. 5c, 15a, 15b). The average contact area of an adherent mouse embryonic stem cell grown on LN-511 was about 2.5 times higher than that of cells plated on non-specific coating like poly-D-lysine (FIG. 15b). Embryonic stem cell spreading on all other coatings, including LN-111, Matrigel and gelatin, was significantly less than on LN-511 or LN-332 (statistical significance P<0.001, Student's two-tailed t-test).

Figure 14A:
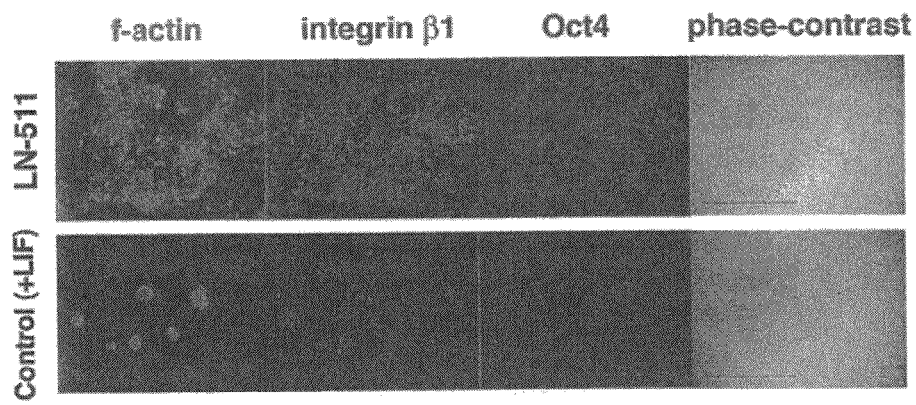
In FIG. 14a, the magnification is 10× and the bar size is 500 µm.
Figure 14B:
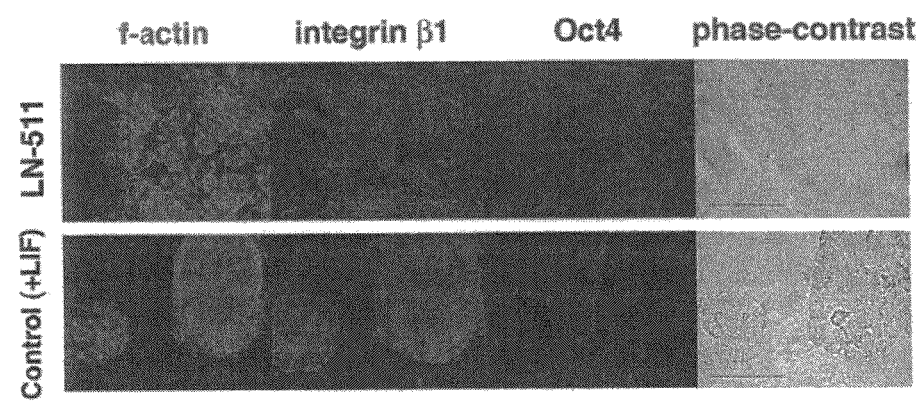
In FIG. 14b, the magnification is 40× and the bar size is 100 µm.

The morphology of mouse embryonic stem cells cultured on LN-511 differed significantly from that of cells cultured in a conventional system, in the presence of LIF, or on mouse fibroblast feeders or gelatin (FIG. 14a, 14b). In these cases, embryonic stem cells formed typical dense clusters with sharp, defined borders. In contrast, mouse embryonic stem cells cultured on LN-511 first formed a monolayer, and started to form multilayers only at high cell density. Apparently the affinity of embryonic stem cells to neighbor cells is lower than that for LN-511, but higher than affinity to conventional extracellular matrix coatings.

Integrin Receptor Expression and Role in Mouse Embryonic Stem Cell Interaction with LN-511.

Figure 16A:
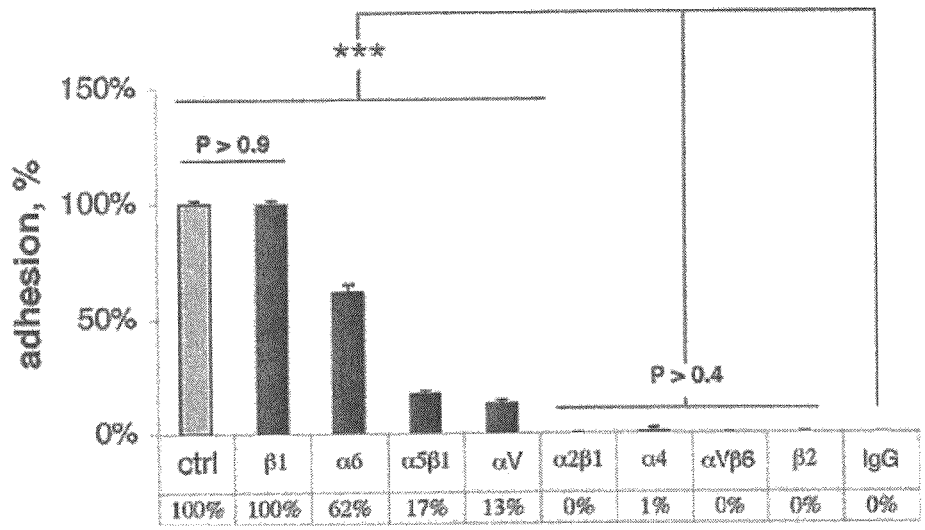
FIGS. 16a-16f are a set of graphs and pictures showing the role of integrin receptors in mouse embryonic stem cell adhesion to LN-511.
Figure 16B:
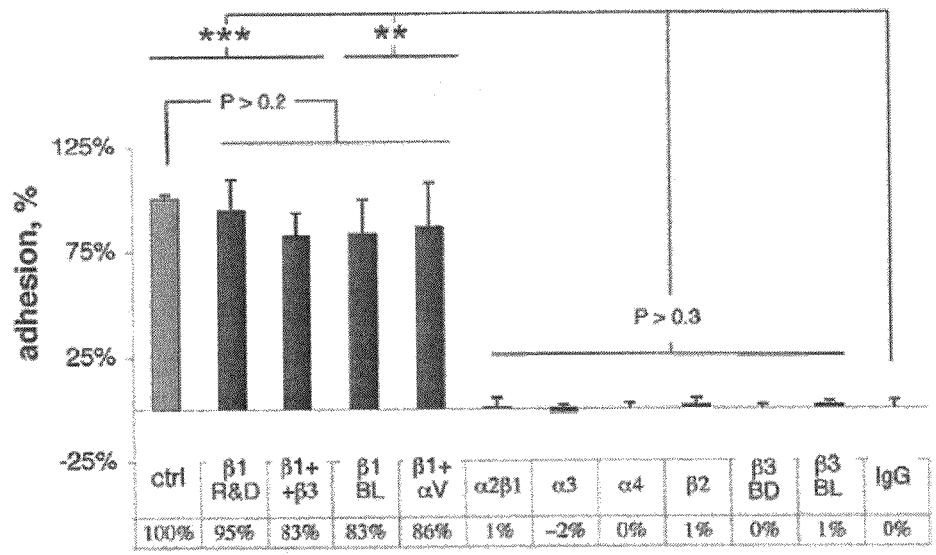

To analyze the complete integrin expression profile in our embryonic stem cells we used Affymetrix arrays. The results are summarized in Table 4, below. However, the Affymetrix array could not reveal which integrin receptors were expressed in sufficient amounts to attach cells to the surface, and which were expressed in minor concentrations. To address that question, we immobilized anti-integrin antibody on a plastic surface and identified specific antibodies that could bind and retain embryonic stem cells attached to the plastic surface (see detailed description in Methods). We found that antibodies against $\beta 1$-integrin retained embryonic stem cells strongly attached to the surface (FIGS. 16a, 16b), while antibody against $\alpha 6$, $\alpha 5\beta 1$ and $\alpha V$ could provide only partial adhesion (60%, 17% and 13%, respectively). Antibodies against $\alpha 2\beta 1$, $\alpha 3$, $\alpha 4$, $\beta 2$, $\beta 3$, $\alpha V\beta 6$ could not retain embryonic stem cells on the surface (FIGS. 16a, 16b).

Figure 16C:
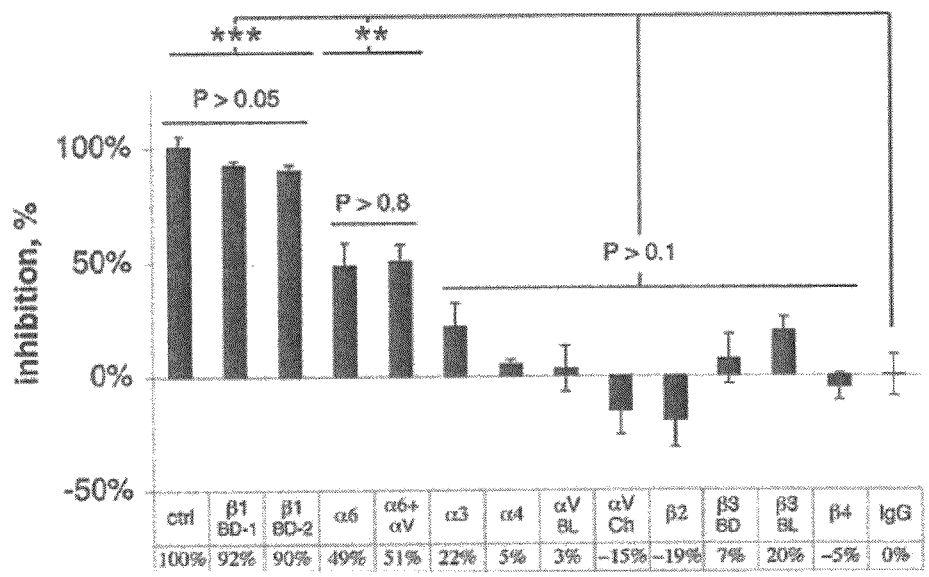
Figure 16D:
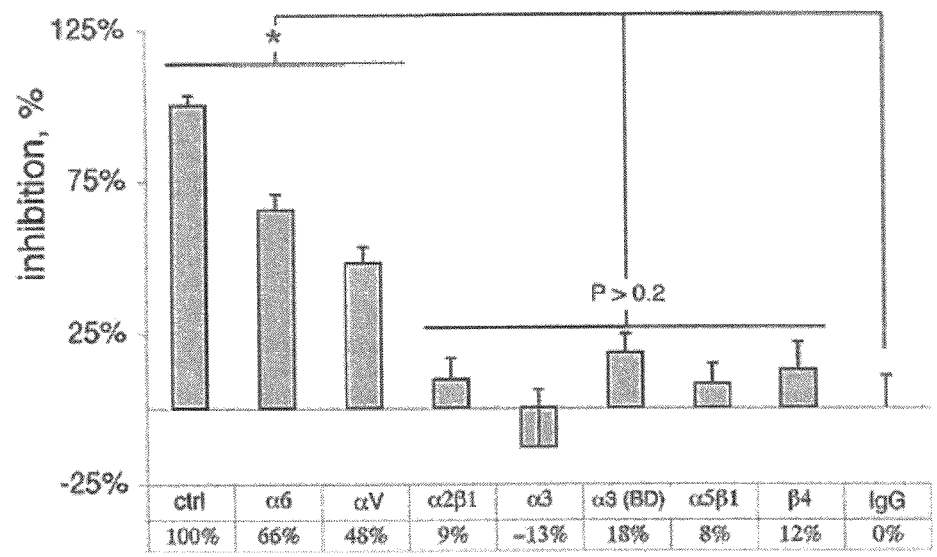
Figure 16E:
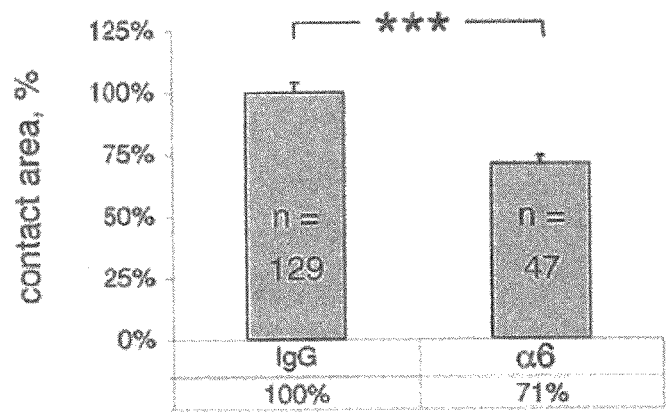

To identify integrin receptors involved in embryonic stem cells interaction with LN-511, we used function-blocking antibodies against specific integrin receptors in the cell adhesion assay. Blocking of $\beta 1$-integrins inhibited mouse embryonic stem cells adhesion to LN-511 completely, as confirmed by two different antibodies (FIG. 16c). Blocking of $\alpha 6$-integrin inhibited mouse embryonic stem cells adhesion to LN-511 only partially, blocking both $\alpha 6$- and $\alpha V$-integrin had the same effect (FIG. 16c). Blocking of $\alpha 2\beta 1$, $\alpha 3$, $\alpha 4$, $\alpha 5\beta 1$, $\alpha V$, $\beta 2$, $\beta 3$ and $\beta 4$-integrins did not affect embryonic stem cells adhesion to LN-511 (FIGS. 16c, 16d). Interestingly, the blocking of $\alpha 6$-integrin significantly decreased the cell contact area with LN-511 coated surface (P<0.001) (FIG. 16e).

Figure 16F:
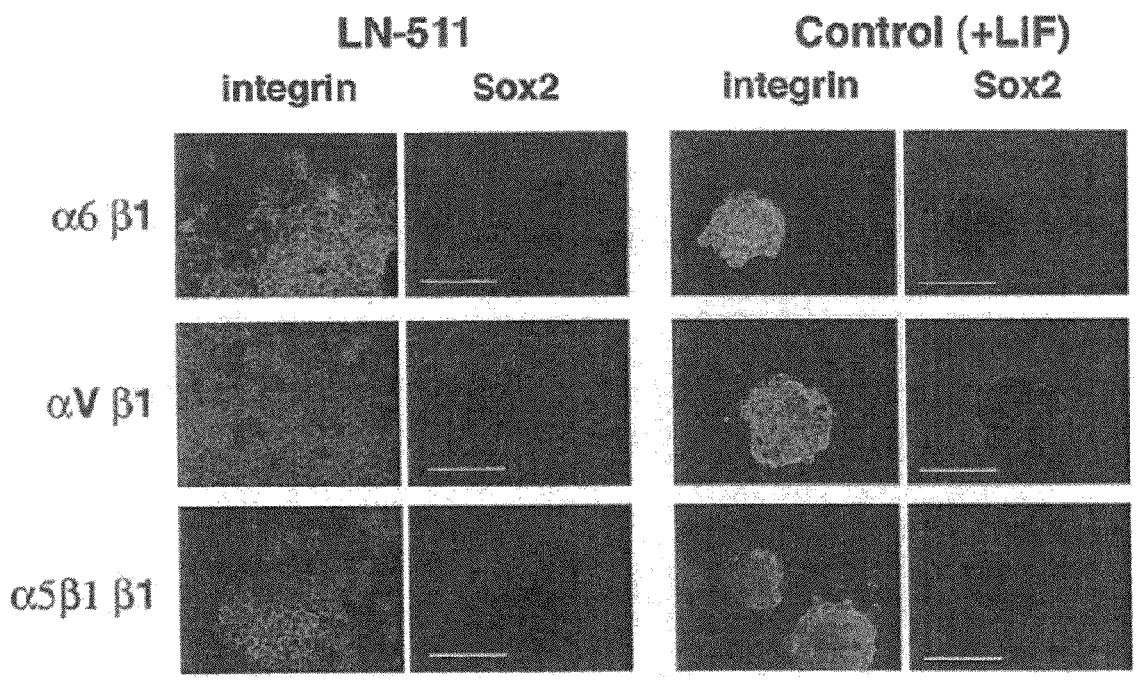
Figure 17:
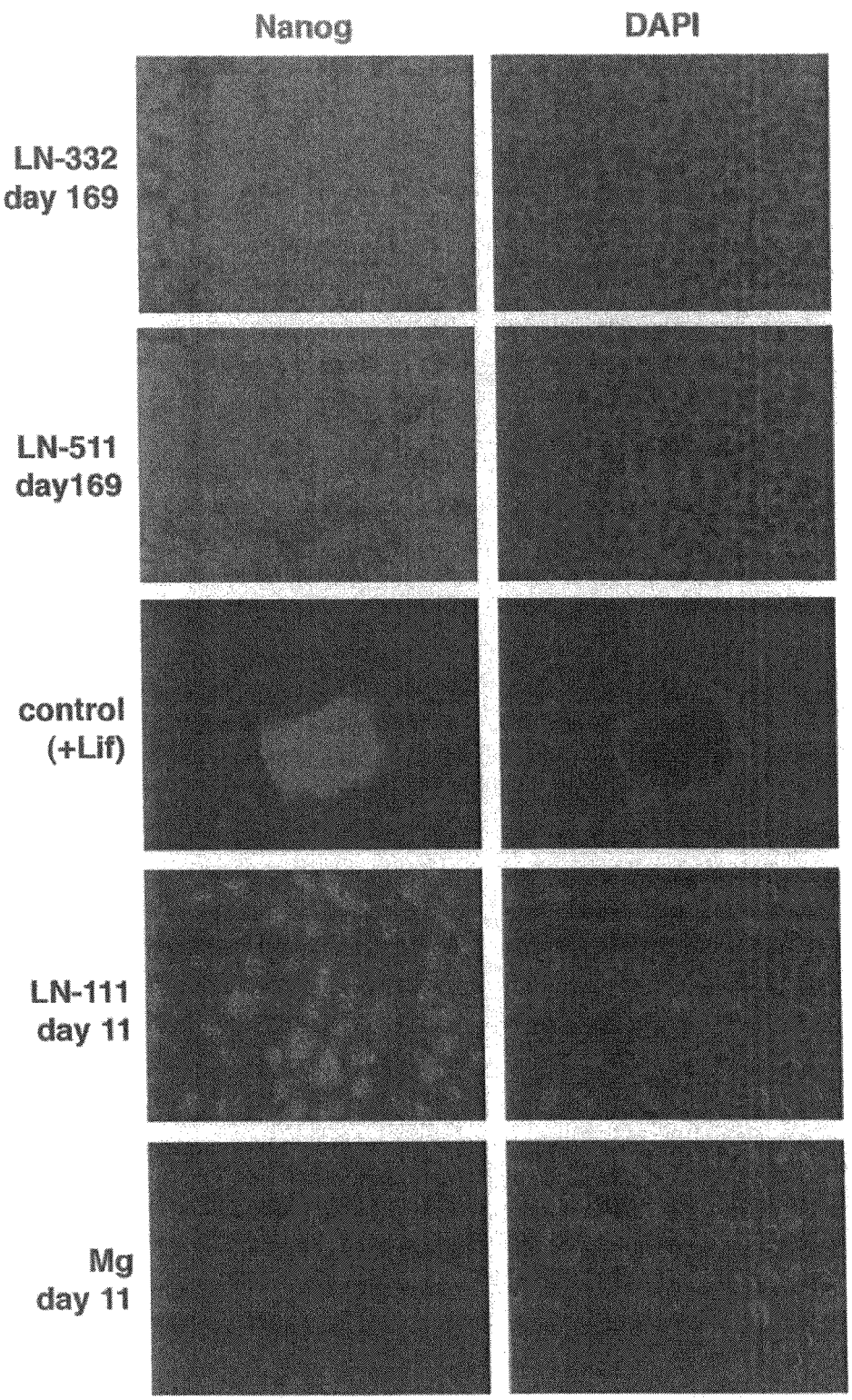
FIG. 17 is a set of pictures showing the immunofluorescent analysis of expression of pluripotency marker Nanog (red) and DNA (DAPI, blue) of mouse embryonic stem cells cultured on LN-332 (169 days), LN-511 (169 days), LN-111 (11 days), and Matrigel™ (Mg, 11 days) in absence of differentiation inhibitors. Cells grown on LN-111 or Matrigel™ were largely or completely differentiated after 11 days in culture, while cells grown on LN-332 or LN-511 or cultured in the presence of LIF maintained expression of Nanog after 169 days. Magnification 40×.
Figure 18:
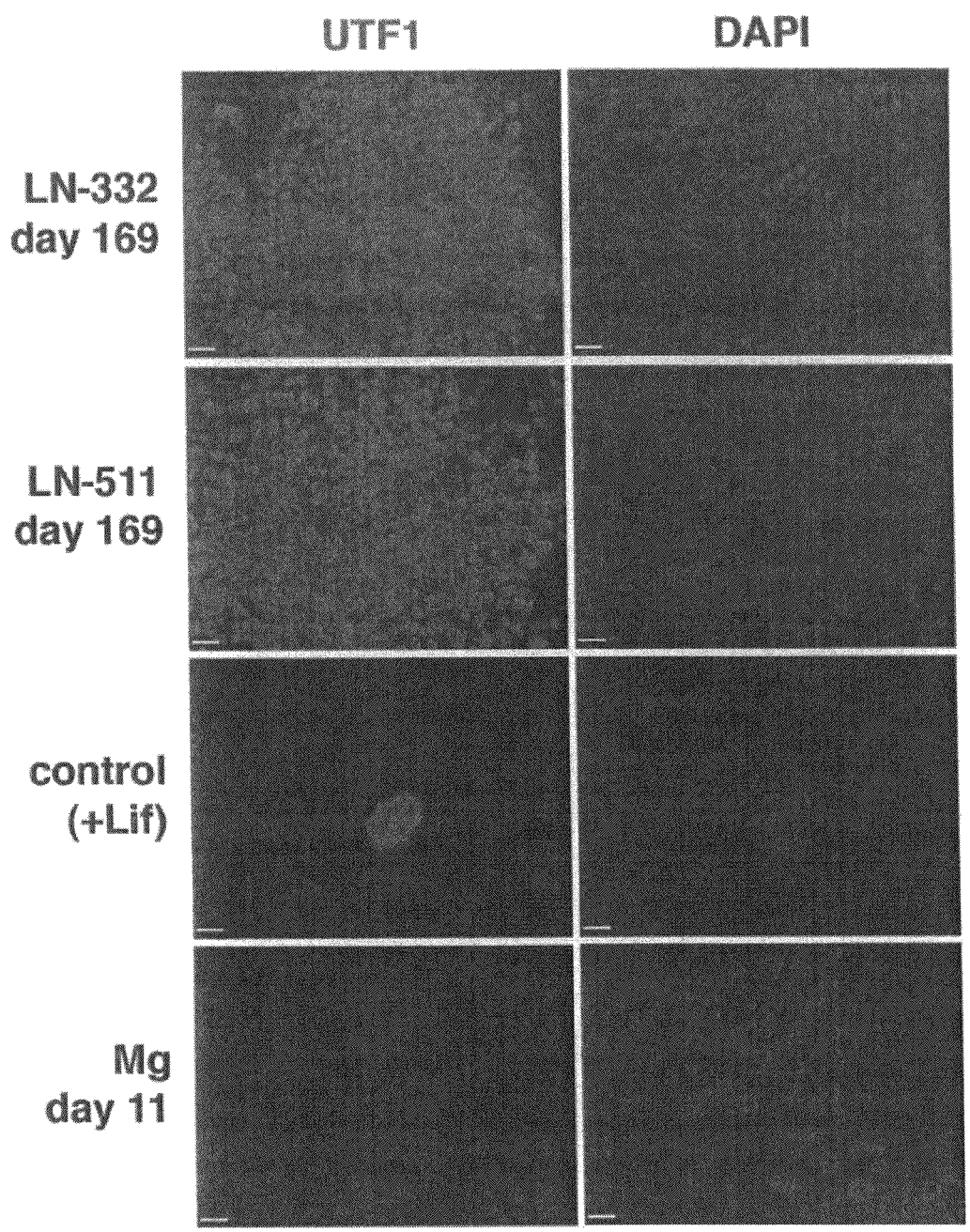
FIG. 18 is a set of pictures showing the immunofluorescent analysis of expression of pluripotency marker UTF1 (red) and DNA (DAPI, blue) of mouse embryonic stem cells cultured on LN-332 (169 days), LN-511 (169 days), and Matrigel™ (Mg, 11 days) in absence of differentiation inhibitors. Cells grown on Matrigel™ were completely differentiated after 11 days in culture, while cells grown on LN-332 or LN-511 or cultured in the presence of LIF maintained expression of UTF1 even up to 169 days in culture. Magnification 40×. Bar size is 27 µm.

Immunofluorescence staining confirmed expression of integrins $\alpha 6\beta 1$, $\alpha V\beta 1$ and $\alpha 5\beta 1$ in pluripotent (Sox2-positive) embryonic stem cells cultured on LN-511 in the absence of inhibitors, as well as embryonic stem cells cultured on gelatin in the presence of LIF (FIG. 16f). Immunostaining also confirmed co-localization of the $\alpha 6$ and $\beta 1$ integrin subunits in both culture systems.

TABLE 4

| IR | Expression, by Affymetrix array | Integrins sufficiently expressed to retain ES cells adherent to surface: | Blocking those integrins inhibits ES cell adhesion to LN-511: | Can form dimers with: |
|---|---|---|---|---|
| $\alpha 1$ | − | n/a | n/a | $\beta 1$ |
| $\alpha 2$ | − | − | − | $\beta 1$ |
| $\alpha 3$ | + | − | − | $\beta 1$ |
| $\alpha 4$ | − | − | − | $\beta 1, \beta 7$ |
| $\alpha 5$ | + | + | − | $\beta 1$ |
| $\alpha 6$ | + | + | + | $\beta 1, \beta 4$ |
| $\alpha 7$ | − | n/a | n/a | $\beta 1$ |

TABLE 4-continued

| IR | Expression, by Affymetrix array | Integrins sufficiently expressed to retain ES cells adherent to surface: | Blocking those integrins inhibits ES cell adhesion to LN-511: | Can form dimers with: |
|---|---|---|---|---|
| α8 | + | n/a | n/a | β1 |
| α9 | + | n/a | n/a | β1 |
| α10 | − | n/a | n/a | β1 |
| α11 | n/a | n/a | n/a | β1 |
| αV | + | + | + | β1, β3, β5, β6, β8 |
| αIIb | + | n/a | n/a | β3 |
| αL | − | n/a | n/a | β2 |
| αM | − | n/a | n/a | β2 |
| αX | − | n/a | n/a | β2 |
| αD | n/a | n/a | n/a | β2 |
| αE | + | n/a | n/a | β7 |
| β1 | + | 100% | 100% | α1, α2, α3, α4, α5, α6, αV |
| β2 | + | − | − | αL, αM, αX, αD |
| β3 | + | − | − | αV, αIIb |
| β4 | − | − | − | α6 |
| β5 | + | n/a | n/a | αV |
| β6 | − | n/a | n/a | αV |
| β7 | + | n/a | n/a | α4, αE |
| β8 | + | n/a | n/a | αV |

Discussion

The results of this second set of experiments showed that a specific laminin isoform, namely LN-511, can support self-renewal of mouse embryonic stem cells for at least 169 days (31 passages) in the absence of feeder cells, or LIF, or other differentiation inhibitors. The effect even occurs at low cell density (<200 cells/mm$^2$). In previous studies, pluripotency of embryonic stem cells has been facilitated by soluble differentiation inhibitors. Moreover, in those studies embryonic stem cells grew in dense clusters that provided each cell multiple contacts with neighbor cells, which was apparently essential to maintain pluripotent status in the presence of differentiation inhibitors. Several previous studies have shown that different combinations of matrix proteins can support pluripotency and self-renewal of embryonic stem cells, however, in combination with soluble differentiation inhibitors. Our results suggest a novel principle, i.e. that contact with certain extracellular matrix molecules can sustain embryonic stem cell pluripotency and proliferation in the absence of differentiation inhibitors and with lack of contact with neighboring embryonic stem cells or feeder cells. We also demonstrated that the effect was laminin-isoform specific.

Notably, there was a striking difference between various laminin isoforms effect on embryonic stem cells. While LN-511 enabled self-renewal, LN-111 triggered differentiation and inhibited proliferation. LN-332 enabled proliferation, but not self-renewal. LN-411 did not support adhesion or survival of embryonic stem cells at all.

As used herein, the term "self-renewal" refers to the ability of the stem cell to go through numerous cycles of cell division and remain undifferentiated (i.e. pluripotent). Pluripotency itself refers to the ability of the stem cell to differentiate into any cell type. The term "proliferation" refers to the ability of the stem cell to divide. Survival refers to the ability of the stem cell to live, whether differentiated or undifferentiated, and does not require the stem cell to maintain its ability to divide or to differentiate.

LN-511 is the most ancient laminin isoform and one of the first laminin isoforms to appear during embryonic development. The laminin α5 chain (LN-511/LN-521), unlike laminin α1 (LN-111/LN-121), has been found in the matrix between cells of the inner cell mass of blastocysts (the in vivo origin of embryonic stem cells). The laminin α1 chain appears in early development and has another ancient progenitor (α1,2 chain in *Drosophila*). It is expressed in the Reichert membrane and some early embryonic basement membranes. Differentiation of non-polar primitive ectoderm into columnar epithelium of the epiblast is induced by LN-111, synthesized by the primitive endoderm. In mice lacking the laminin α1 chain LG4-5 domain, presumptive epiblast cells failed to polarize and did not survive past day 6.5, which demonstrates that this domain provides vital signals for the conversion of stem cells to polarized epithelium.

Notably, ability of LN-511 and LN-332 to support embryonic stem cell proliferation correlated with strong adhesion of the embryonic stem cells to those two laminins. This observation agrees with previously published data, proving that cell proliferation is strongly dependent on cell contact area with adhesive substratum. From an evolutionary standpoint, the laminin α3 and α5 chains have the same progenitor (α3,5 chain in *Drosophila*), which may explain the partial similarity of their effect on embryonic stem cells.

Without being bound by theory, it appears that mouse embryonic stem cells interact with LN-511 via β1-integrins, as we proved that blocking of β1-integrins completely inhibits embryonic stem cell adhesion to LN-511. Of all β1-integrins, α6β1 seems to be the main integrin receptor involved in interaction with LN-511, but not the only one. αVβ1 integrin may also contribute to adhesion, however, blocking of both α6 and αV still did not provide complete inhibition or any synergistic effect. It appears that α8β1, α9β1 or α11β1 may contribute to adhesion, but function-blocking antibodies for those a-subunits were not available.

In our study we used human laminins (LN-332, LN-411 and LN-511) with mouse embryonic stem cells. Sequence analysis shows that the sequence similarity between human and mouse species for the α-chains of those laminins is high (77%, 88% and 78%, respectively). Notably, sequence similarity between α-chains of those human laminins is significantly lower (below 35%).

A major problem concerning the use of extracellular matrix proteins for technological purposes is the lack of availability of pure native isoforms for such purposes. At the present, mouse EHS sarcoma derived LN-111 is the only laminin isoform commercially available in pure native form for cell culture use. Protease-solubilized laminins from human placenta have been shown to contain a mixture of more or less degraded LN-211, LN-411 or LN-511, that can yield variable and irreproducible results.

The present study has, however, demonstrated that human recombinant laminins can be used to develop defined cell culturing systems for mouse embryonic stem cells. It was demonstrated that LN-511 possesses differentiation inhibitory activity that allows the cells to preserve pluripotency even if they lack contacts with neighboring cells and are deprived of soluble differentiation inhibitors. Recombinant human laminins may become a useful tool for stem cell research, as they can be used to generate defined coating substrata. This applies particularly to the establishment and expansion of human pluripotent stem cells that need to be cultured in xeno-free defined environments if they are to be used for the purpose of human cell therapy.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A composition that enables self-renewal of pluripotent stem cells grown in vitro, comprising a substrate including a beta fibroblast growth factor (bFGF) and only one single laminin isoform, wherein the single laminin isoform is recombinant laminin 511 (laminin-10) and the pluripotent stem cells are mouse pluripotent embryonic stem cells, human pluripotent embryonic stem cells, or human induced pluripotent stem (iPS) cells.

2. The composition of claim 1, wherein the composition is devoid of any differentiation inhibitors.

3. The composition of claim 1, wherein the composition is devoid of any feeder cells.

4. The composition of claim 1, wherein the composition is devoid of any differentiation inductors.

5. The composition of claim 1, wherein the composition is devoid of any differentiation inhibitors, feeder cells, and differentiation inductors.

6. The composition of claim 1, wherein the pluripotent stem cells are human iPS cells.

7. A method for maintaining the pluripotency of pluripotent stem cells in vitro, comprising:
providing a substrate including only one single laminin isoform, wherein the single laminin isoform is recombinant laminin 511(laminin-10);
placing the pluripotent stem cells on the substrate, wherein the pluripotent stem cells are mouse pluripotent embryonic stem cells, human pluripotent embryonic stem cells, or human induced pluripotent stem (iPS) cells;
exposing the pluripotent stem cells to a growth medium comprising beta fibroblast growth factor (bFGF); and
culturing the pluripotent stem cells.

8. The method of claim 7, wherein the growth medium and the substrate are devoid of any differentiation inhibitors.

9. The method of claim 7, wherein the composition is devoid of any feeder cells.

10. The method of claim 7, wherein the composition is devoid of any differentiation inductors.

11. The method of claim 7, wherein the composition is devoid of any differentiation inhibitors, feeder cells, and differentiation inductors.

12. The method of claim 7, wherein the pluripotent stem cells are placed on the coating as a monolayer.

13. The method of claim 7, wherein the pluripotent stem cells are placed on the coating at a density of 200 cells $mm^2$ or less.

14. The method of claim 7, wherein the pluripotent stem cells are mouse pluripotent embryonic stem cells, and wherein the pluripotent stem cells are placed on the coating so that each stem cell does not contact another stem cell.

15. The method of claim 7, wherein the pluripotent stem cells are human pluripotent embryonic stem cells.

16. The method of claim 7, wherein the pluripotent stem cells are human iPS cells.

17. A composition that enables self-renewal of pluripotent stem cells grown in vitro, comprising a substrate consisting essentially of beta fibroblast growth factor (bFGF) and only one single laminin isoform, wherein the single laminin isoform is recombinant laminin 511(laminin-10) and the pluripotent stem cells are mouse pluripotent embryonic stem cells, human pluripotent embryonic stem cells, or human induced pluripotent stem (iPS) cells.

18. A composition that enables self-renewal of pluripotent stem cells grown in vitro, consisting of a substrate including beta fibroblast growth factor (bFGF) and a single laminin isoform which is recombinant laminin 511 (laminin-10), wherein the pluripotent stem cells are mouse pluripotent embryonic stem cells, human pluripotent embryonic stem cells, or human induced pluripotent stem (iPS) cells.

* * * * *